US008580764B2

(12) United States Patent
Abbadessa et al.

(10) Patent No.: US 8,580,764 B2
(45) Date of Patent: Nov. 12, 2013

(54) COMBINATIONAL COMPOSITIONS AND METHODS FOR TREATMENT OF CANCER

(75) Inventors: Giovanni Abbadessa, Boston, MA (US); Dennis S. France, Winchester, MA (US); Chang-Rung Chen, Newton, MA (US); Thomas C. K. Chan, Winchester, MA (US)

(73) Assignee: ArQule, Inc., Woburn, MA (US)

( * ) Notice: Subject to any disclaimer, the term of this patent is extended or adjusted under 35 U.S.C. 154(b) by 230 days.

(21) Appl. No.: 13/174,890

(22) Filed: Jul. 1, 2011

(65) Prior Publication Data

US 2012/0004191 A1 Jan. 5, 2012

Related U.S. Application Data

(60) Provisional application No. 61/360,758, filed on Jul. 1, 2010, provisional application No. 61/475,995, filed on Apr. 15, 2011.

(51) Int. Cl.
| *A01N 43/04* | (2006.01) |
| *A61K 31/70* | (2006.01) |
| *A01N 43/62* | (2006.01) |
| *A61K 31/55* | (2006.01) |
| *A61K 31/535* | (2006.01) |
| *A01N 43/42* | (2006.01) |
| *A61K 31/44* | (2006.01) |

(52) U.S. Cl.
USPC ........... 514/49; 514/220; 514/233.5; 514/294

(58) Field of Classification Search
None
See application file for complete search history.

(56) References Cited

U.S. PATENT DOCUMENTS

| 4,522,811 | A | 6/1985 | Eppstein et al. | |
| 7,713,969 | B2 | 5/2010 | Li et al. | |
| 8,216,571 | B2 * | 7/2012 | Ramachandra et al. | ... 424/130.1 |
| 8,304,425 | B2 * | 11/2012 | Wang et al. | ................... 514/294 |
| 8,377,927 | B2 * | 2/2013 | Li et al. | ......................... 514/220 |
| 2006/0223760 | A1 | 10/2006 | Li et al. | |
| 2010/0221251 | A1 | 9/2010 | Li et al. | |
| 2010/0297075 | A1 | 11/2010 | Chan et al. | |
| 2011/0104256 | A1 * | 5/2011 | Wang et al. | ................... 424/450 |
| 2012/0052062 | A1 | 3/2012 | Chen et al. | |

FOREIGN PATENT DOCUMENTS

| WO | WO-2006086484 A1 | 8/2006 |
| WO | WO-2008127710 A2 | 10/2008 |
| WO | WO-2009002806 A1 | 12/2008 |
| WO | WO-2010093789 A2 | 8/2010 |

OTHER PUBLICATIONS

Laux et al. "Phase I Dose Escalation Trial (ARQ 197-11) Evaluating Combination of Selective c-Met Inhibitor ARQ 197 and Erlotinib." *J. Clin. Oncol.* 27.15S(2009). (Abstract #3549).
Schiller et al. "Results from ARQ 197-209: A Global Randomized Placebo-Controlled Phase II Clinical Trial of Erlotinib Plus ARQ 197 Versus Erlotinib Plus Placebo in Previously Treated EGFR Inhibito-Naive Patients with Locally Advanced or Metastatic Non-Small Cell Lung Cancer (NSCLC)." *J. Clin. Oncol.* 28.18S(2010). (Abstract #LBA7502).
Arora et al. The Journal of Pharmacology and Experimental Therapeutics, 2006, vol. 316, No. 3, pp. 971-979.
Cappuzzo et al. "Epidermal Growth Factor Receptor Gene and Protein and Gefitinib Sensitivity in Non-Small-Cell Lung Cancer." *J. Natl. Cancer Inst.* 97.9(2005):643-655.
Cappuzzo et al. "Increased MET Gene Copy Number Negatively Affects Survival of Surgically Resected Non-Small-Cell Lung Cancer Patients." *J. Clin. Oncol.* 27.10(2009):1667-1674.
Comoglio et al. "Drug Development of MET Inhibitors: Targeting Oncogene Addiction and Expedience." *Nat. Rev. Drug Disc.* 7.6(2008):504-516.
Go et al. "High MET Gene Copy No. Leads to Shorter Survival in Patients With Non-Small Cell Lung Cancer." *J. Thorac. Oncol.* 5.3(2010):305-313.
Jackman et al. "Impact of Epidermal Growth Factor Receptor and KRAS Mutations on Clinical Outcomes in Previously Untreated Non-Small Cell Lung Cancer Patients: Results of an Online Tumor Registry of Clinical Trials." *Clin. Cancer Res.* 15.16(2009):5267-5273.
Li et al. "An Improved Protocol for the Preparation of 3-Pyridyl-and Some Arylboronic Acids." *J. Org. Chem.* 67(2002):5394-5397.
Massarelli et al. "KRAS Mutation is an Important Predictor of Resistance to Therapy With Epidermal Growth Factor Receptor Tyrosine Kinase Inhibitors in Non-Small-Cell Lung Cancer." *Clin. Cancer Res.* 13.10(2007):2890-2896.
Pao et al. "EGF Receptor Gene Mutations are Common in Lung Cancers From "Never Smokers" and are Associated With Sensitivity of Tumors to Gefitinib and Erlotinib." *PNAS.* 101.36(2004):13306-13311.
Registry Data for Tivantinib (Registry No. 905854-02-6, Accessed Apr. 19, 2012).
Rosell et al. "Screening for Epidermal Growth Factor Receptor Mutations in Lung Cancer." *N. Engl. J. Med.* 361.10(2009):958-967.
Shepherd et al. "Erlotinib in Previously Treated Non-Small-Cell Lung Cancer." *N. Engl. J. Med.* 353.2(2005):123-132.
Therasse et al. "New Guidelines to Evaluate the Response to Treatment in Solid Tumors." *J. Natl. Cancer Inst.* 92.3(2000):205-216.
Bardelli et al., "Gab1 coupling to the HGF/Met receptor multifunctional docking site requires binding of Grb2 and correlates with the transforming potential", *Oncogene*, 15:3103-3111 (1997).

(Continued)

*Primary Examiner* — Lawrence E Crane
(74) *Attorney, Agent, or Firm* — Mintz Levin Cohn Ferris Glovsky and Popeo, P.C.; Ivor R. Elrifi; Matthew Pavao

(57) ABSTRACT

The present invention provides methods of treating a cell proliferative disorder, such as lung cancer and breast cancer, by administering to a subject in need thereof a therapeutically effective amount of a pyrroloquinolinyl-pyrrole-2,5-dione compound or a pyrroloquinolinyl-pyrrolidine-2,5-dione compound, such as (−)-trans-3-(5,6-dihydro-4H-pyrrolo[3,2,1-ij]quinolin-1-yl)-4-(1H-indol-3-yl)pyrrolidine-2,5-dione, in combination with a therapeutically effective amount of a second anti-proliferative agent, such as gemcitabine.

17 Claims, 20 Drawing Sheets

(56) References Cited

OTHER PUBLICATIONS

Beviglia et al., "Expression of the c-Met/HGF Receptor in Human Breast Carcinoma: Correlation with Tumor Progression", *Int. J. Cancer*, 74:301-309 (1997).

Birchmeier et al., "Met, Metastasis, Motility and More", *Nature Rev.*, 4:915-925 (2003).

Cerqueira et al. "Understanding ribonucleotide reductase inactivation by gemcitabine." *Chemistry—A European Journal*, vol. 13, Issue 30, pp. 8507-8515 (2007).

Chou, T. C., "The Median-Effect Principle and the Combination Index for Quantitation of Synergism and Antagonism", in *Synergism and Antagonism in Chemotherapy*, Eds., Chou & Rideout, Academic Press, Inc., San Diego, Ch. 2, pp. 61-102 (1991).

Cooper et al., "Molecular cloning of a new transforming gene from a chemically transformed human cell line", *Nature*, 311:29-33 (1984).

Danilkovitch-Miagkova et al., "Dysregulation of Met receptor tyrosine kinase activity in invasive tumors", *J. Clin. Invest.*, 109:863-867 (2002).

Hughes, D. L., "The Mitsunobu Reaction", in *Organic Reactions*, John Wiley & Sons, Inc., vol. 42, Ch. 2, pp. 335-395 (1992).

Li et al., "An Improved Protocol for the Preparation of 3-Pyridyl-and Some Arylboronic Acids", *J. Org. Chem.*, 67:5394-5397 (2002).

Li et al., "Selective killing of cancer cells by β-lapachone: Direct checkpoint activation as a strategy against cancer", *Proc. Natl. Acad. Sci. U.S.A.*, 100(5):2674-2678 (2003).

Ma et al., "c-Met: Structure, functions and potential for therapeutic inhibitions", *Cancer Metast. Rev.*, 22:309-325 (2003).

Marson et al., "Highly efficient syntheses of 3-aryl-2-cycloalken-1-ones and an evaluation of their liquid crystalline properties", *Tetrahedron*, 59:4377-4381 (2003).

Mark et al., "Combination efficacy with MetMAb and erlotinib in NSCLC tumor model highlight therapeutic opportunities for c-Met inhibitors in combination with EGFR inhibitors", *99th AACR Annual Meeting*, 49:313-314 (Apr. 12-16, 2008) (Abstract Only).

Mitsunobu et al., "Stereospecific and Stereoselective Reactions. I. Preparation of Amines from Alcohols", *J. Am. Chem. Soc.*, 94:679-680 (1972).

Nakajima et al., "The Prognostic Significance of Amplification and Overexpression of c-*met* and c-*erb* B-2 in Human Gastric Carcinomas", *Cancer*, 85:1894-1902 (1999).

Puri et al., "Synergism of EGFR and c-Met pathways, cross-talk and inhibition, in non-small cell lung cancer", *J. Carcinogenesis*, 7:9 (2008) (8 pages).

Qian et al., "Met Protein Expression Level Correlates with Survival in Patients with Late-stage Nasopharyngeal Carcinoma", *Cancer Res.*, 62:589-596 (2002).

Qiao et al., "Constitutive Activation of Met Kinase in Non-Small-Cell Lung Carcinomas Correlates With Anchorage-Independent Cell Survival", *J. Cell. Biochem.*, 86:665-677 (2002).

Rosen et al., "A Phase 1 dose escalation study of ARQ 197, a selective inhibitor of the c-Met receptor in patients with metastatic solid tumors", *Eur. J. Cancer*, 4:196 (Abstract Only), Nov. 2006.

Seiwert et al., "The MET receptor tyrosine kinase is a potential novel therapeutic target for head and neck squamous cell carcinoma", *Cancer Res.*, 69(7):3021-3031 (2009).

Takayama et al., "Diverse tumorigenesis associated with aberrant development in mice overexpressing hepatocyte growth factor/scatter factor", *Proc. Natl. Acad. Sci. U.S.A.*, 94:701-706 (1997).

Takeuchi et al., "c-MET Expression Level in Primary Colon Cancer: A Predictor of Tumor Invasion and Lymph Node Metastases", *Clin. Cancer Res.*, 9:1480-1488 (2003).

Tang et al., "Dual MET-EGFR combinatorial inhibition against T790M-EGFR-mediated erlotinib-resistant lung cancer", *Br. J. Cancer*, 99:911-922 (2008).

Thurlimann et al., "Management of Primary Breast Cancer: An Update", *Onkologie*, 27:175-179 (2004).

Traxler et al., "Tyrosine Kinase Inhibitors: From Rational Design to Clinical Trials", *Med. Res. Rev.*, 21(6):499-512 (2001).

Weidner et al., "The Met Receptor Tyrosine Kinase Transduces Motility, Proliferation, and Morphogenic Signals of Scatter Factor/Hepatocyte Growth Factor in Epithelial Cells", *J. Cell Biol.*, 121(1):145-154 (1993).

Zhang et al., "Met decoys: Will cancer take the bait?", *Cancer Cell*, 5-6 (2004).

\* cited by examiner

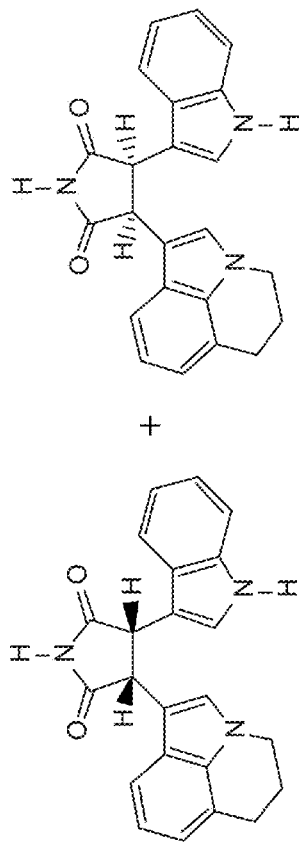
(±)-cis-3-(5,6-dihydro-4H-pyrrolo [3,2,1-ij] quinolin-1yl)-4(1H-indol-3-yl) pyrrolidine-2, 5-dione
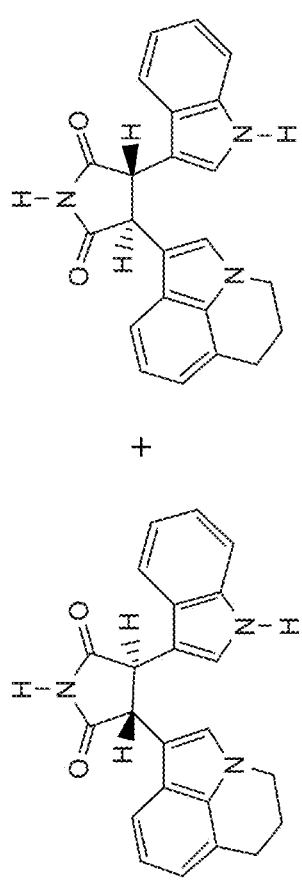
(+)-trans-3-(5,6-dihydro-4H-pyrrolo [3,2,1-ij] quinolin-1-yl)-4(1H-indol-3-yl) pyrrolidine-2, 5-dione.
(−)-trans-3-(5,6-dihydro-4H-pyrrolo [3,2,1-ij] quinolin-1-yl)-4(1H-indol-3-yl) pyrrolidine-2, 5-dione.
FIG. 1

$$CI = \frac{C_A^{mix}}{C_A^0} + \frac{C_B^{mix}}{C_B^0}$$

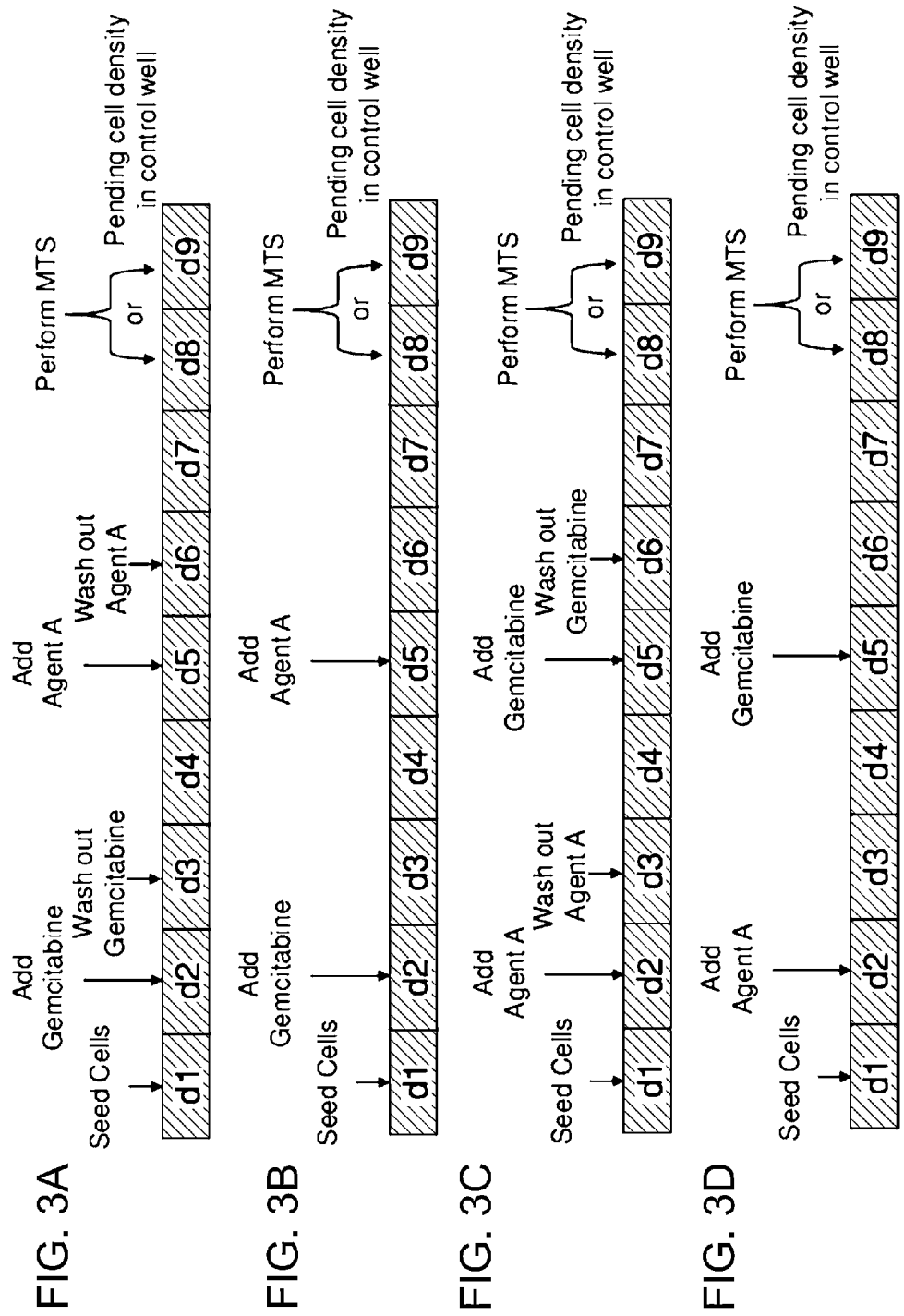

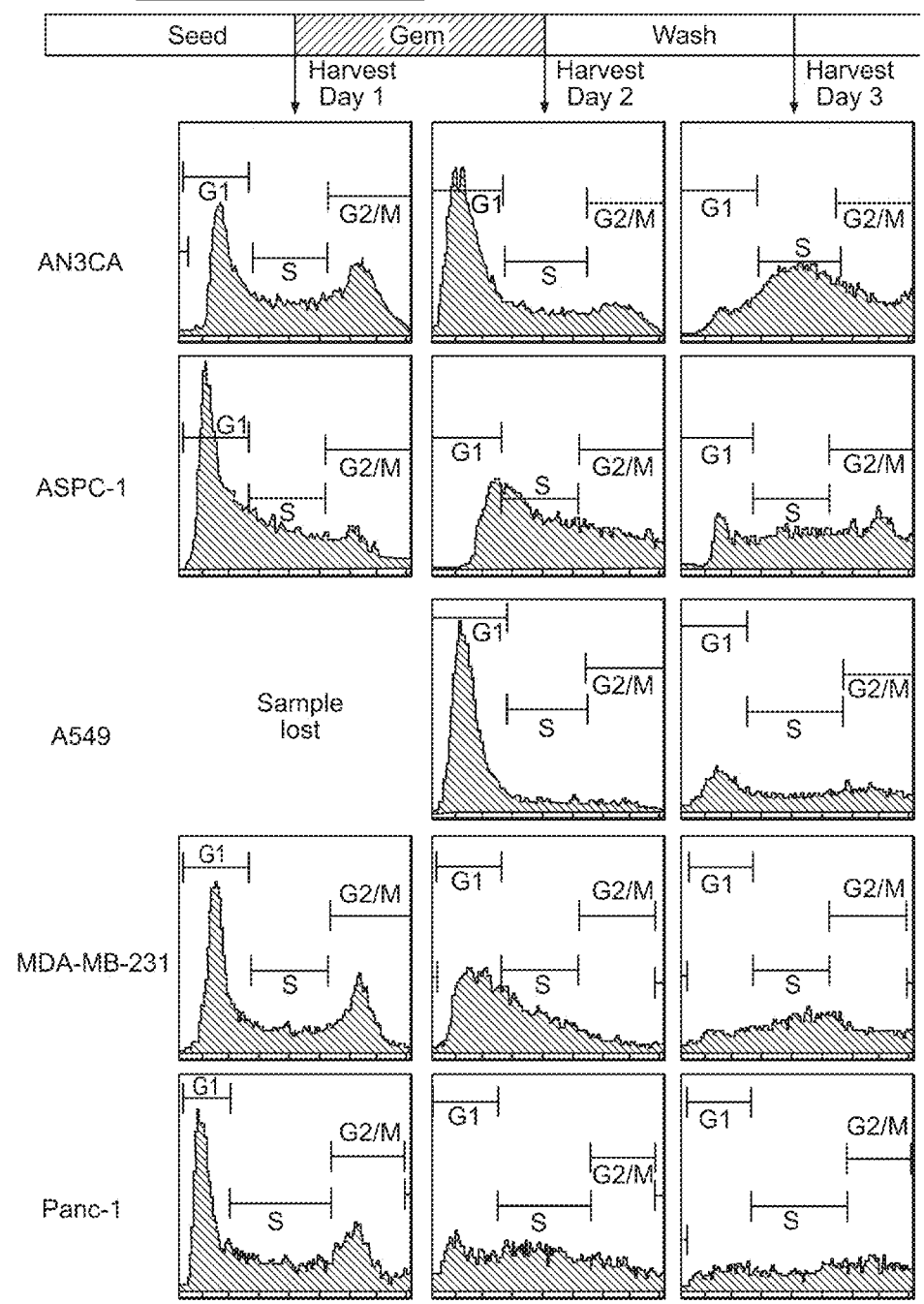

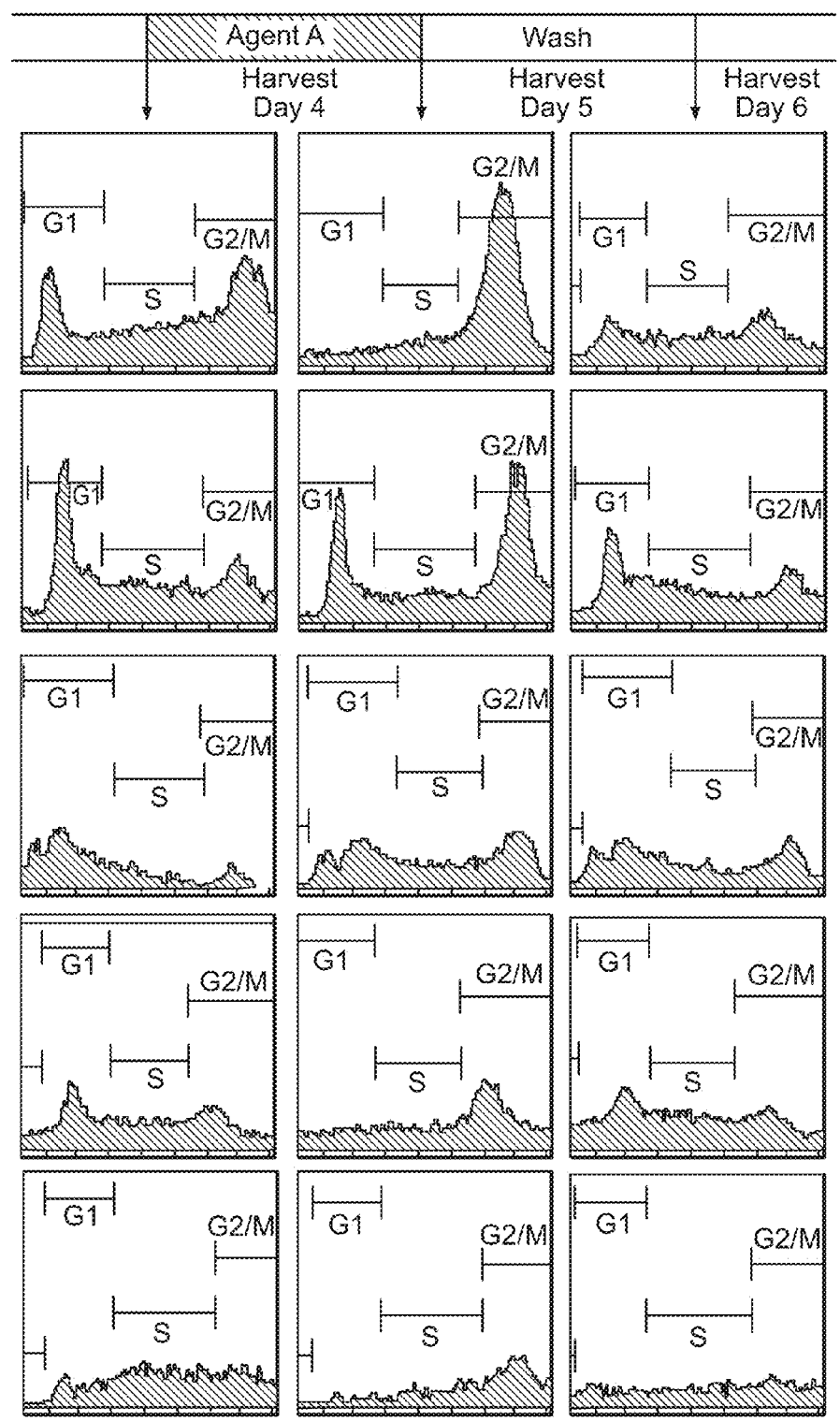

FIG. 8C
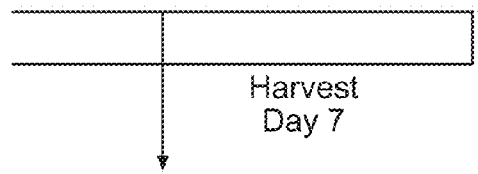
Harvest
Day 7
Sample
lost
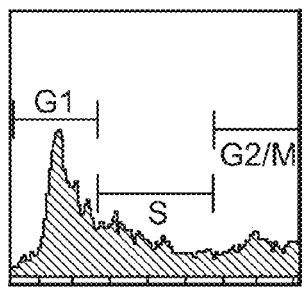
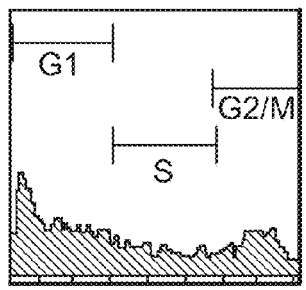
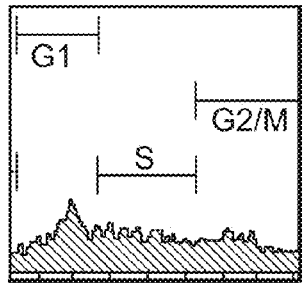
Sample
lost

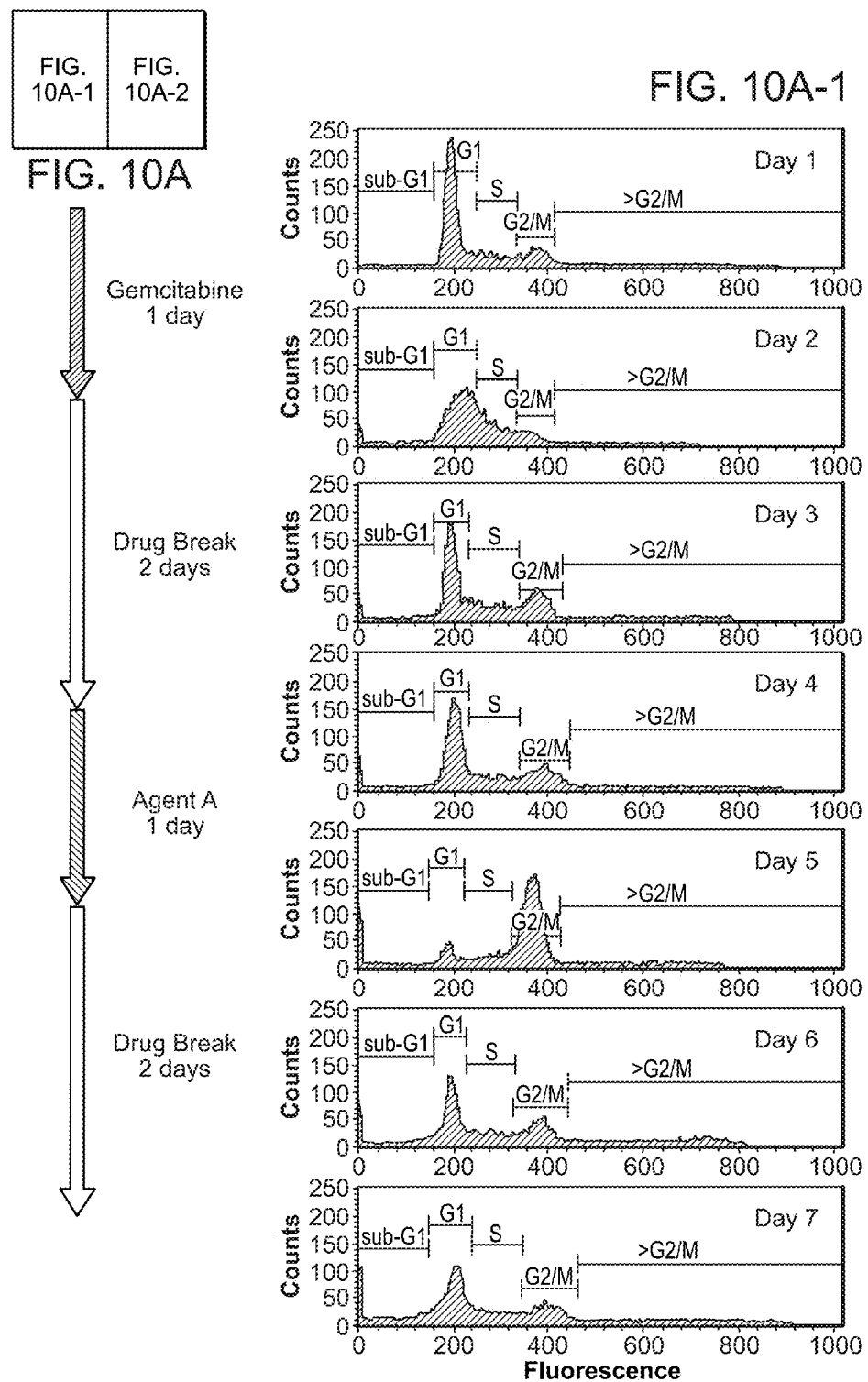

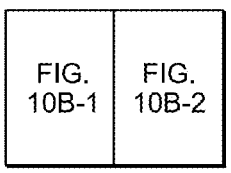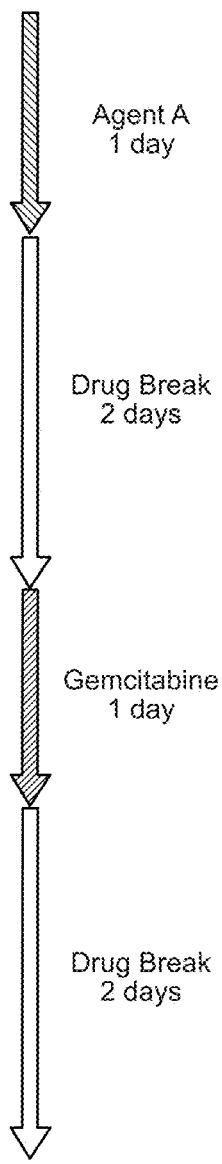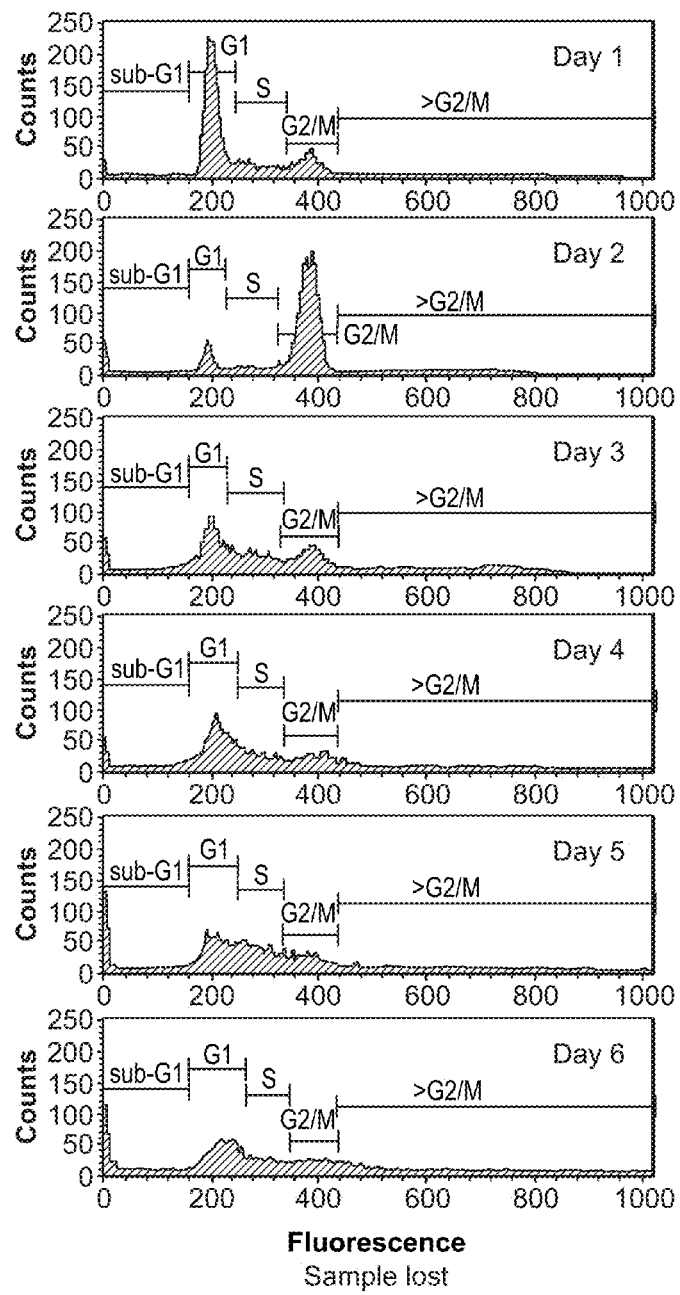

COMBINATIONAL COMPOSITIONS AND METHODS FOR TREATMENT OF CANCER

CROSS REFERENCE TO RELATED APPLICATIONS

This application claims priority to, and the benefit of, U.S. Provisional Application No. 61/360,758, filed Jul. 1, 2010 and U.S. Provisional Application No. 61/475,995, filed Apr. 15, 2011. The content of these applications are incorporated herein by reference in its entirety.

BACKGROUND OF THE INVENTION

Cancer is the second leading cause of death in the United States, exceeded only by heart disease. (*Cancer Facts and Figures* 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same histiotype that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemias). It is therefore often difficult to predict whether a particular cancer will respond to a particular chemotherapeutic agent. (*Cancer Medicine,* 5th Edition, Bast et al. eds., B. C. Decker Inc., Hamilton, Ontario)

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extracellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are dysregulated in human cancers, and may contribute to dysregulation of cell growth, tumor cell dissemination, and tumor invasion during disease progression and metastasis. (See, e.g., *Journal of Clinical Investigation* 109: 863-867 (2002) and *Cancer Cell* pp 5-6 July 2004) c-Met and HGF are highly expressed relative to surrounding tissue in numerous cancers, and their expression correlates with poor patient prognosis. (See, e.g., *Journal of Cellular Biochemistry* 86: 665-677 (2002); *Int. J. Cancer (Pred. Oncol.)* 74: 301-309 (1997); *Clinical Cancer Research* 9: 1480-1488 (2003); and *Cancer Research* 62: 589-596 (2002)) Without intending to be bound by theory, c-Met and HGF may protect tumors against cell death induced by DNA damaging agents, and as such may contribute to chemoresistance and radioresistance of tumors. Without intending to be limited by any theory, inhibitors of c-Met may be useful as therapeutic agents in the treatment of proliferative disorders including breast cancer. (See, e.g., *Cancer and Metastasis Reviews* 22: 309-325 (2003))

The references cited herein are not admitted to be prior art to the claimed invention.

SUMMARY OF THE INVENTION

The present invention provides a method of treating a cell proliferative disorder, the method comprising administering to a subject a therapeutically effective amount of a compound of formula III, IIIa, IVa, IVb, Va, or Vb, or a pharmaceutically acceptable salt thereof, or a prodrug or metabolite thereof, in combination with a therapeutically effective amount of a second anti-proliferative agent, wherein the compound of formula III, IIIa, IVa, IVb, Va, or Vb, or a pharmaceutically acceptable salt thereof, or a prodrug or metabolite thereof, and the second anti-proliferative agent are not administered concurrently.

The present invention also provides a method of treating a cell proliferative disorder, the method comprising administering to a subject a therapeutically effective amount of a compound of formula III, IIIa, IVa, IVb, Va, or Vb, or a pharmaceutically acceptable salt thereof, or a prodrug or metabolite thereof, in combination with a therapeutically effective amount of a second anti-proliferative agent, wherein the compound of formula III, IIIa, IVa, IVb, Va, or Vb, or a pharmaceutically acceptable salt thereof, or a prodrug or metabolite thereof, is administered after the administration of the second anti-proliferative agent.

The present invention also provides a method of treating a cell proliferative disorder, the method comprising administering to a subject a therapeutically effective amount of a compound of formula III, IIIa, IVa, IVb, Va, or Vb, or a pharmaceutically acceptable salt thereof, or a prodrug or metabolite thereof, in combination with a therapeutically effective amount of a second anti-proliferative agent, wherein the second anti-proliferative agent is administered after the administration of the compound of formula III, IIIa, IVa, IVb, Va, or Vb, or a pharmaceutically acceptable salt thereof, or a prodrug or metabolite thereof.

The compound of formula III, IIIa, IVa, IVb, Va, or Vb can be (+)-cis-3-(5,6-dihydro-4H-pyrrolo[3,2,1-ij]quinolin-1-yl)-4-(1H-indol-3-yl)pyrrolidine-2,5-dione, (−)-cis-3-(5,6-dihydro-4H-pyrrolo[3,2,1-ij]quinolin-1-yl)-4-(1H-indol-3-yl)pyrrolidine-2,5-dione, (+)-trans-3-(5,6-dihydro-4H-pyrrolo[3,2,1-ij]quinolin-1-yl)-4-(1H-indol-3-yl)pyrrolidine-2,5-dione, or (−)-trans-3-(5,6-dihydro-4H-pyrrolo[3,2,1-ij]quinolin-1-yl)-4-(1H-indol-3-yl)pyrrolidine-2,5-dione. Preferably, the compound is (−)-trans-3-(5,6-dihydro-4H-pyrrolo[3,2,1-ij]quinolin-1-yl)-4-(1H-indol-3-yl)pyrrolidine-2,5-dione.

The second anti-proliferative agent can be a a kinase inhibitor, an alkylating agent, an antibiotic, an anti-metabolite, a detoxifying agent, an interferon, a polyclonal or monoclonal antibody, a HER2 inhibitor, a histone deacetylase inhibitor, a hormone, a mitotic inhibitor, an MTOR inhibitor, a taxane or taxane derivative, an aromatase inhibitor, an anthracycline, a microtubule targeting drug, a topoisomerase poison drug, an adenosine analogue drug, a guanosine analogue drug, a methyluridine analogue drug, or a cytidine analogue drug. Preferably, the cytidine analogue is gemcitabine. Preferably, the kinase inhibitor is serine/threonine kinase inhibitor or a tyrosine kinase inhibitor. Preferred kinase inhibitors include, but are not limited to, sorafenib, sunitinib, erlotinib, imatinib, and gefitinib. Preferred alkylating agents include, but are not limited to, cisplatin or carboplatin. Preferred anti-metabolites include, but are not limited to, gemcitabine, fluorouracil (5-FU), TS-1 or capecitabine. Preferred mitotic inhibitors include, but are not limited to, camptothecin or irinotecan. Preferred taxane or taxane derivatives include, but are not limited to, paclitaxel or docetaxel.

The cell proliferative disorder can be a precancerous condition or cancer. The cell proliferative disorder can be a hematologic tumor or malignancy, or a solid tumor (or tumors). The methods of treating cancer include a reduction in tumor size. Alternatively, or in addition, the cancer is metastatic cancer and this method of treatment includes inhibition of metastatic cancer cell invasion. The method can further include radiation therapy. The cancer can be lung cancer, small cell lung cancer, non-small cell lung cancer (NSCLC), colon cancer, breast cancer, pancreatic cancer, prostate cancer, renal cancer, cervical cancer, brain cancer, gastric/stomach cancer, uterine cancer, intestinal cancer, hepatic cancer, chronic myelogenous leukemia, melanoma, ovarian cancer, translocation-associated renal cell carcinoma (RCC), alveolar soft part sarcoma (ASPS), clear cell sarcoma (CCS), or hepatocellular carcinoma (HCC).

Cells with a proliferative disorder can contain DNA encoding c-Met. Alternatively, or in addition, cells with a proliferative disorder have a constitutively enhanced c-Met activity. Preferably, the cell proliferative disease is cancer, and particularly those cancers which express c-Met at high levels or express active c-Met. Thus, the present invention provides a method of treating cell proliferative disorders where the cells express c-Met at high levels or express active c-Met. The present invention further provides a method of treating a cell proliferative disorder comprising selectively modulating an activity of c-Met, without significantly inhibiting the activity of Protein Kinase C.

Preferably, the subject is a mammal. More preferably, the subject is a human.

Preferably, the compound of formula III, IIIa, IVa, IVb, Va, or Vb of the methods described herein is (−)-trans-3-(5,6-dihydro-4H-pyrrolo[3,2,1-ij]quinolin-1-yl)-4-(1H-indol-3-yl)pyrrolidine-2,5-dione and is administered at a dose of 360 mg, provided twice a day. Alternatively, the composition is administered at a maximal daily dose of 720 mg.

Preferably, the the compound of formula III, IIIa, IVa, IVb, Va, or Vb and the second anti-proliferative agent are administered intravenously, orally or intraperitoneally. The second anti-proliferative agent can be administered preceding administration of, or following administration of the composition comprising the compound of formula III, IIIa, IVa, IVb, Va, or Vb.

Preferably, the compound of formula III, IIIa, IVa, IVb, Va, or Vb is (−)-trans-3-(5,6-dihydro-4H-pyrrolo[3,2,1-ij]quinolin-1-yl)-4-(1H-indol-3-yl)pyrrolidine-2,5-dione and the second anti-proliferative agent is gemcitabine and the (−)-trans-3-(5,6-dihydro-4H-pyrrolo[3,2,1-ij]quinolin-1-yl)-4-(1H-indol-3-yl)pyrrolidine-2,5-dione is administered at least 12 hours after the administration of gemcitabine. The (−)-trans-3-(5,6-dihydro-4H-pyrrolo[3,2,1-ij]quinolin-1-yl)-4-(1H-indol-3-yl)pyrrolidine-2,5-dione can also be administered at least 24 hours, at least 48 hours, at least 72 hours or at least 96 hours after the administration of gemcitabine.

Preferably, the subject has not been administered any drug for at least 12 hours, at least 24 hours or at least 48 hours prior to administration of gemcitabine.

Preferably, the subject is not administered any drug for at least 24 hours, is then administered gemcitabine for no more than 24 hours, and is then administered (−)-trans-3-(5,6-dihydro-4H-pyrrolo[3,2,1-ij]quinolin-1-yl)-4-(1H-indol-3-yl)pyrrolidine-2,5-dione for at least 72 hours.

Preferably, the gemcitabine is administered in a single dose, is administered for no more than 30 minutes, no more than 1 hour, no more than 12 hours or for no more than 24 hours. Preferably, the (−)-trans-3-(5,6-dihydro-4H-pyrrolo[3,2,1-ij]quinolin-1-yl)-4-(1H-indol-3-yl)pyrrolidine-2,5-dione is administered for at least 24 hours, at least 48 hours or at least 72 hours.

Preferably, the compound of formula III, IIIa, IVa, IVb, Va, or Vb is (−)-trans-3-(5,6-dihydro-4H-pyrrolo[3,2,1-ij]quinolin-1-yl)-4-(1H-indol-3-yl)pyrrolidine-2,5-dione is administered after the concentration or amount of the gemcitabine in said subject is less than about 90%, less than about 50%, less than about 20%, less than about 10%, less than about 5%, or less than about 1% of its starting concentration or amount.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE FIGURES

FIG. 1 sets forth the chemical structures of (±)-cis-3-(5,6-dihydro-4H-pyrrolo[3,2,1-ij]quinolin-1-yl)-4-(1H-indol-3-yl)pyrrolidine-2,5-dione and (±)-trans-3-(5,6-dihydro-4H-pyrrolo[3,2,1-ij]quinolin-1-yl)-4-(1H-indol-3-yl)pyrrolidine-2,5-dione.

FIG. 2A shows the Combination Index (CI) calculation and FIG. 2B shows an isobologram analysis graph.

FIG. 3 shows the dosing regimens for (−)-trans-3-(5,6-dihydro-4H-pyrrolo[3,2,1-ij]quinolin-1-yl)-4-(1H-indol-3-yl)pyrrolidine-2,5-dione/gemcitabine combinations.

FIG. 8 is a cell cycle analysis of dosing regimen A presented in FIG. 3, showing S-phase arrest in response to gemcitabine treatment and G2/M arrest in response to (−)-trans-3-(5,6-dihydro-4H-pyrrolo[3,2,1-ij]quinolin-1-yl)-4-(1H-indol-3-yl)pyrrolidine-2,5-dione treatment.

DETAILED DESCRIPTION OF THE INVENTION

1. Methods of Treatment

Figures 2A, 2B:
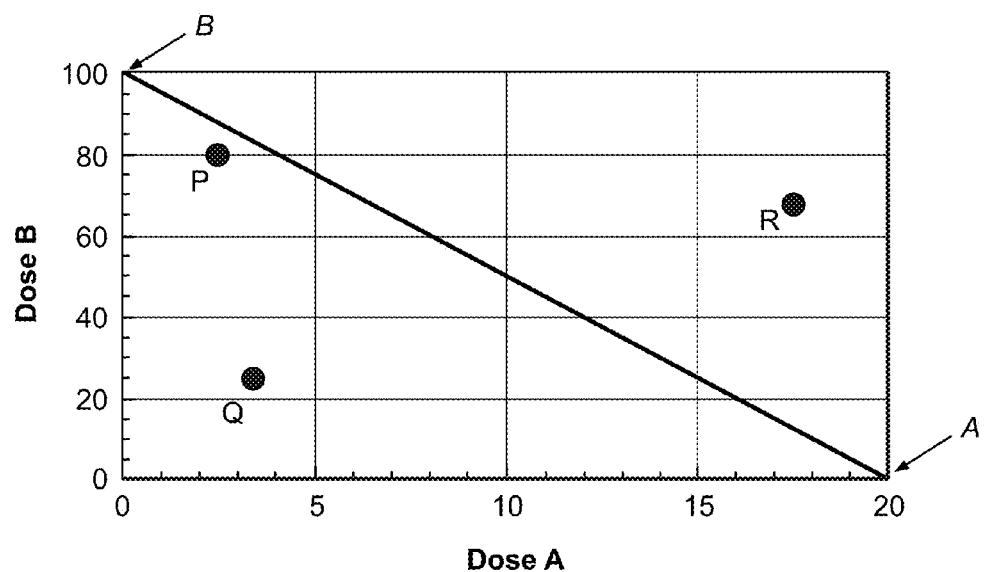
FIG. 2A-B is a depiction of the computational tools used to assess pharmacologic synergy.
Figure 4A:
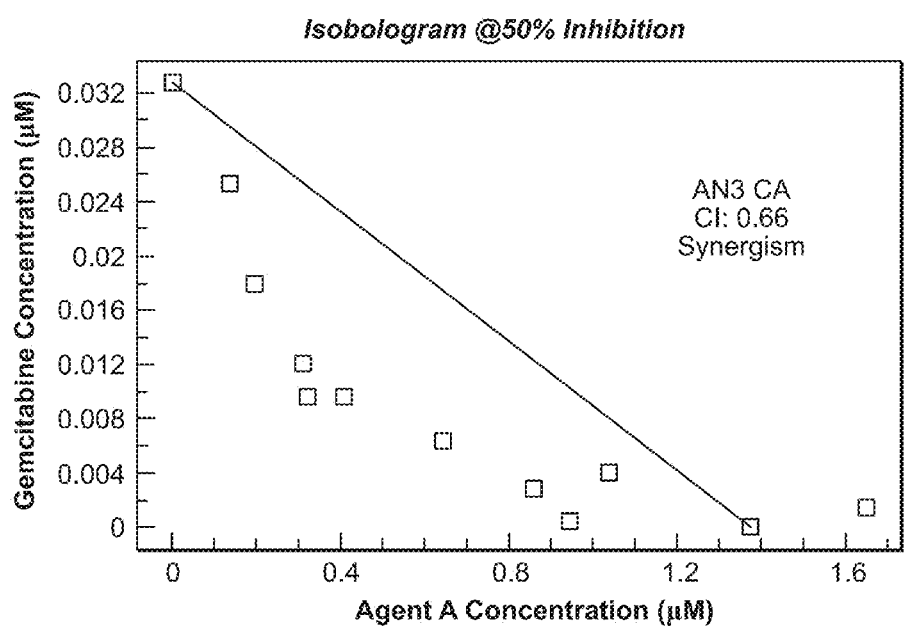
FIG. 4 shows the isobolograms of gemcitabine treatment followed by (−)-trans-3-(5,6-dihydro-4H-pyrrolo[3,2,1-ij]quinolin-1-yl)-4-(1H-indol-3-yl)pyrrolidine-2,5-dione treatment with wash-out of gemcitabine.
Figure 4B:
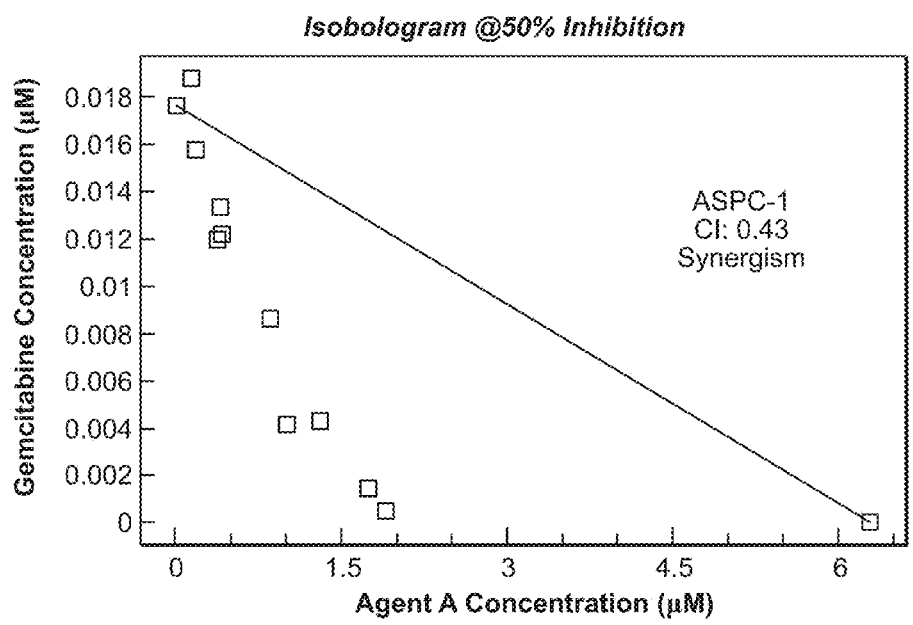
Figure 4C:
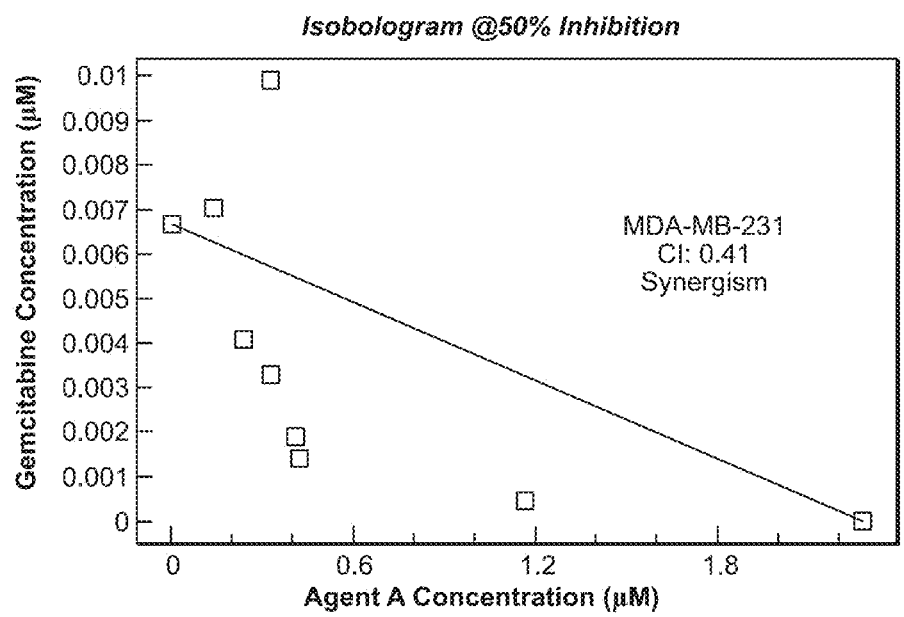
Figure 4D:
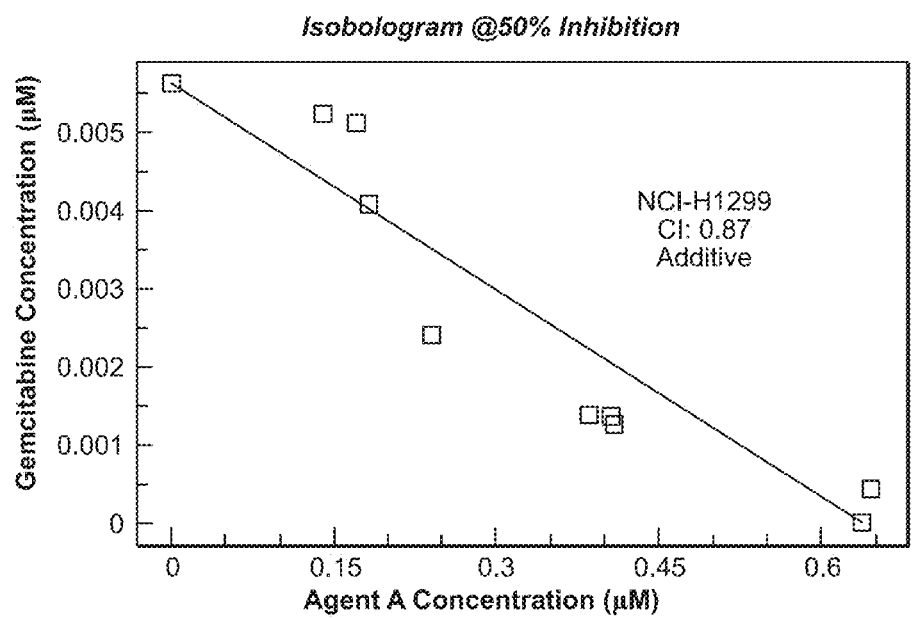
Figure 5A:
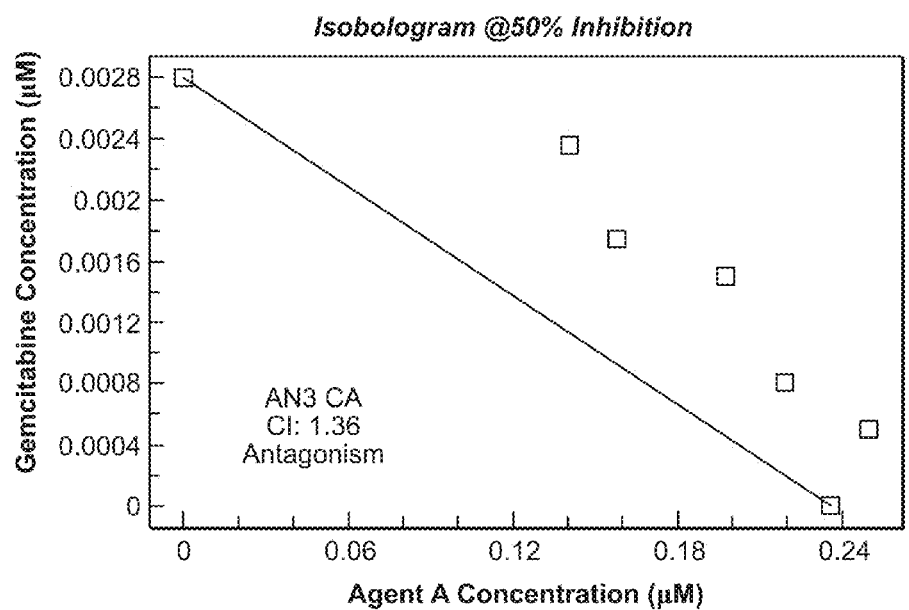
FIG. 5 shows the isobolograms of gemcitabine treatment followed by (−)-trans-3-(5,6-dihydro-4H-pyrrolo[3,2,1-ij]quinolin-1-yl)-4-(1H-indol-3-yl)pyrrolidine-2,5-dione treatment without wash-out of gemcitabine.
Figure 5B:
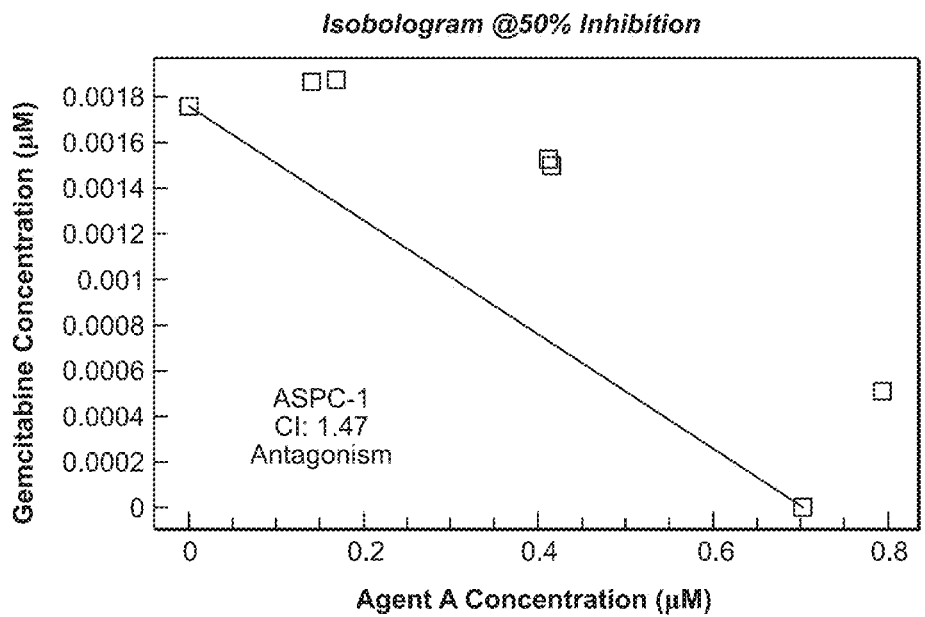
Figure 5C:
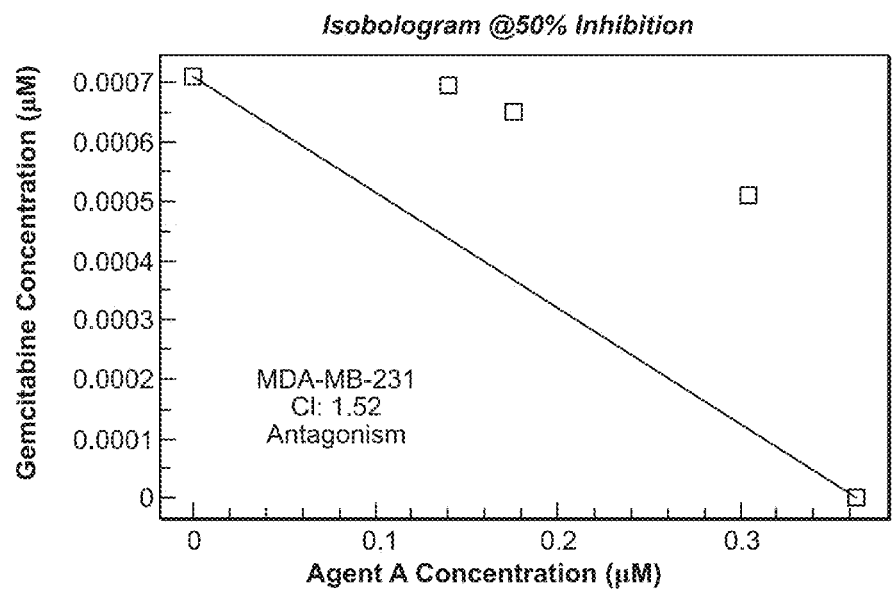
Figure 5D:
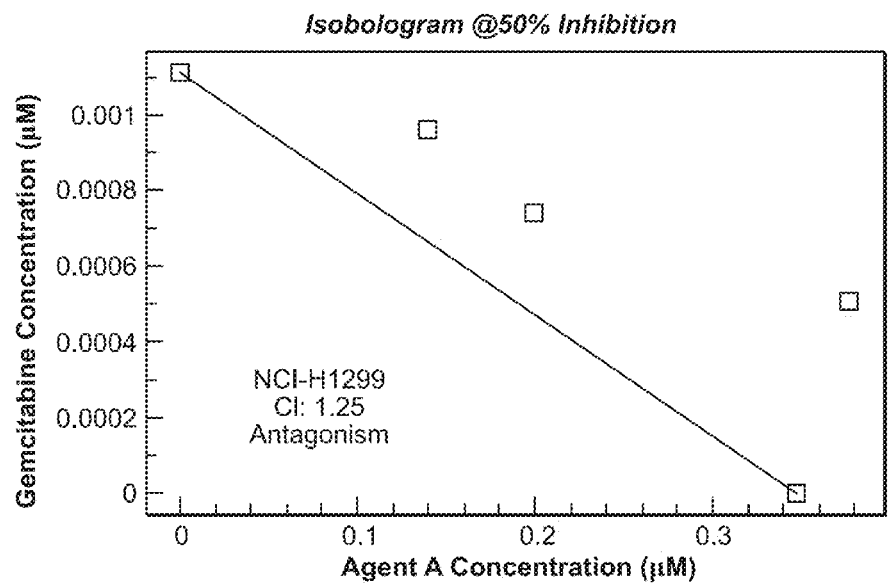
Figure 6A:
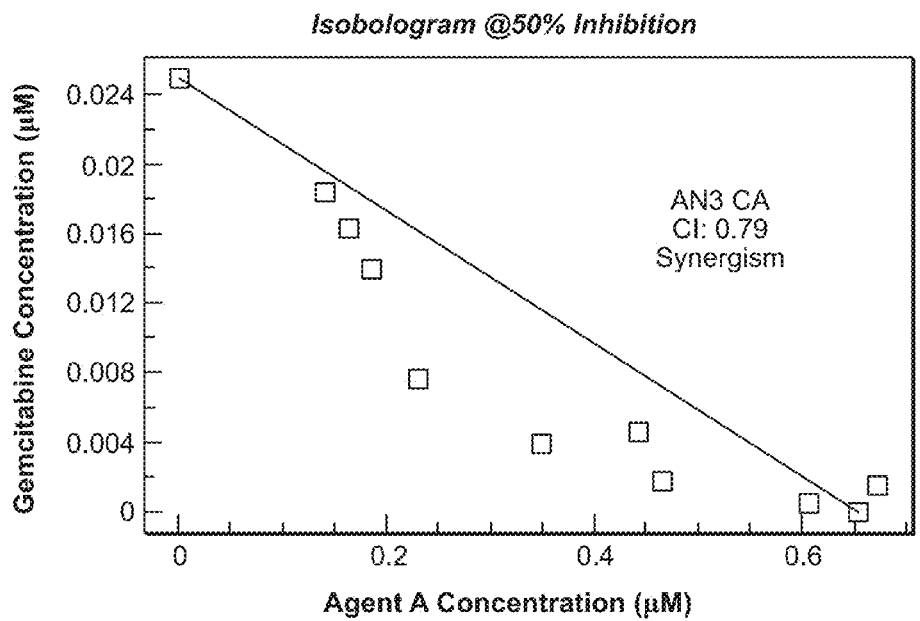
FIG. 6 shows the isobolograms of (−)-trans-3-(5,6-dihydro-4H-pyrrolo[3,2,1-ij]quinolin-1-yl)-4-(1H-indol-3-yl)pyrrolidine-2,5-dione treatment followed by gemcitabine treatment with wash-out of (−)-trans-3-(5,6-dihydro-4H-pyrrolo[3,2,1-ij]quinolin-1-yl)-4-(1H-indol-3-yl)pyrrolidine-2, 5-dione.
Figure 6B:
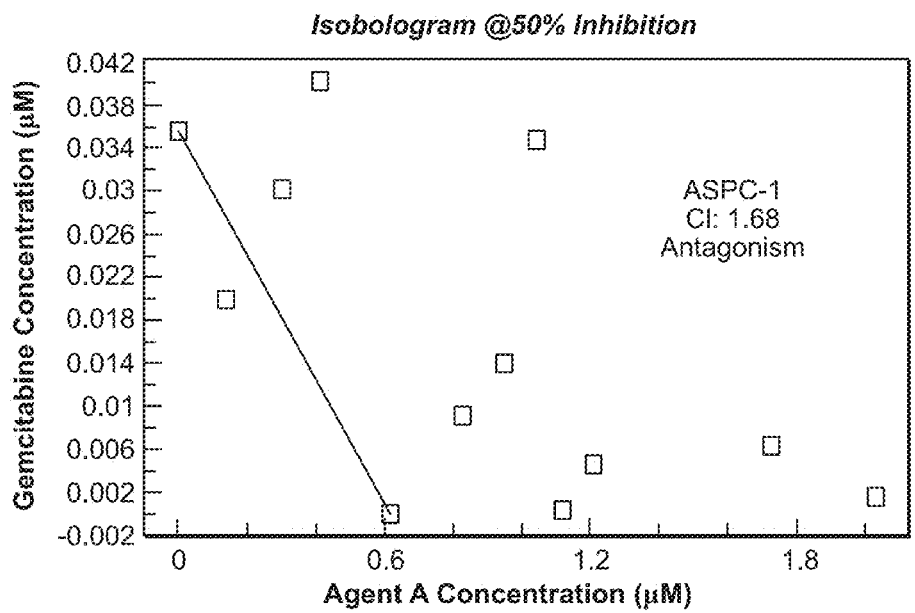
Figure 6C:
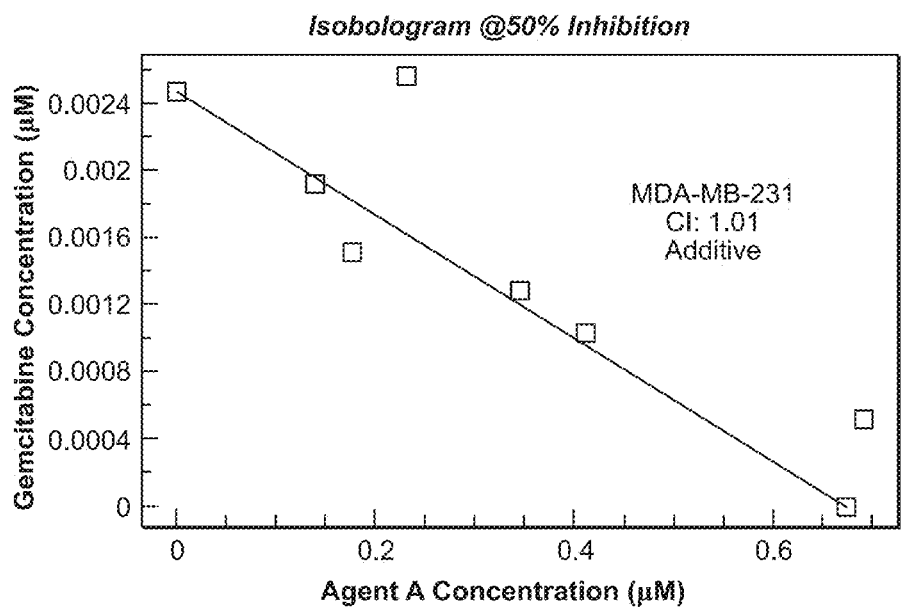
Figure 6D:
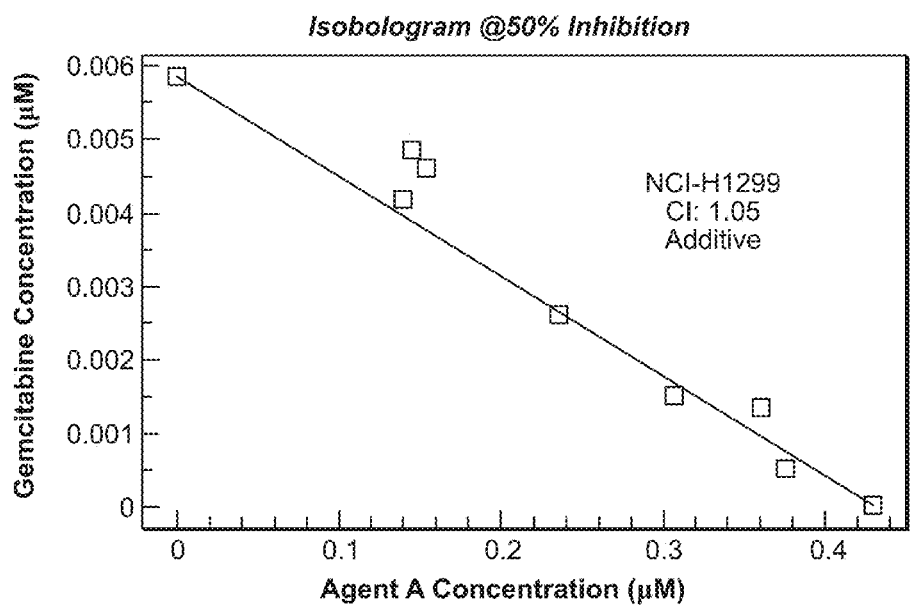
Figure 7A:
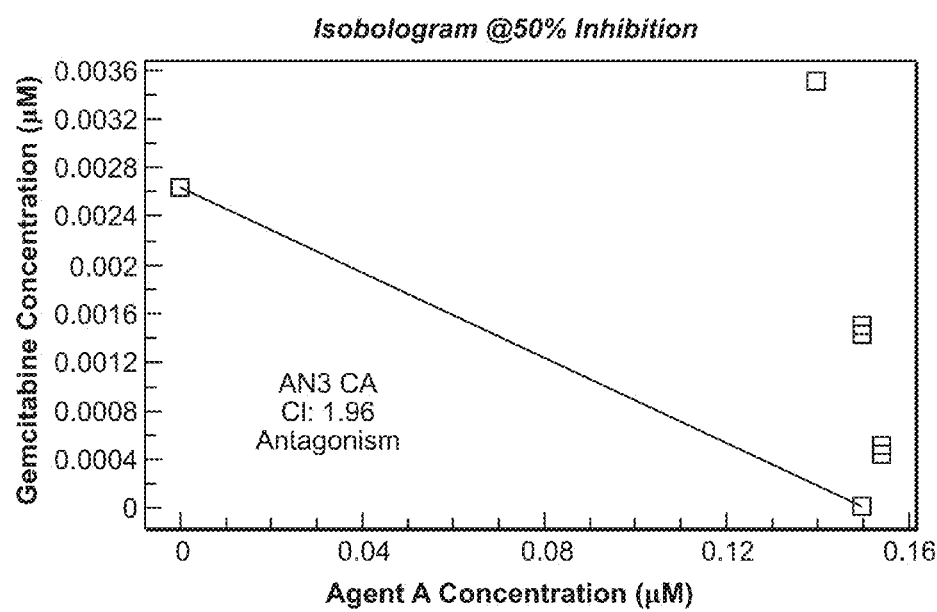
FIG. 7 shows the isobolograms of (−)-trans-3-(5,6-dihydro-4H-pyrrolo[3,2,1-ij]quinolin-1-yl)-4-(1H-indol-3-yl) pyrrolidine-2,5-dione treatment followed by gemcitabine treatment without wash-out of (−)-trans-3-(5,6-dihydro-4H-pyrrolo[3,2,1-ij]quinolin-1-yl)-4-(1H-indol-3-yl)pyrrolidine-2,5-dione.
Figure 7B:
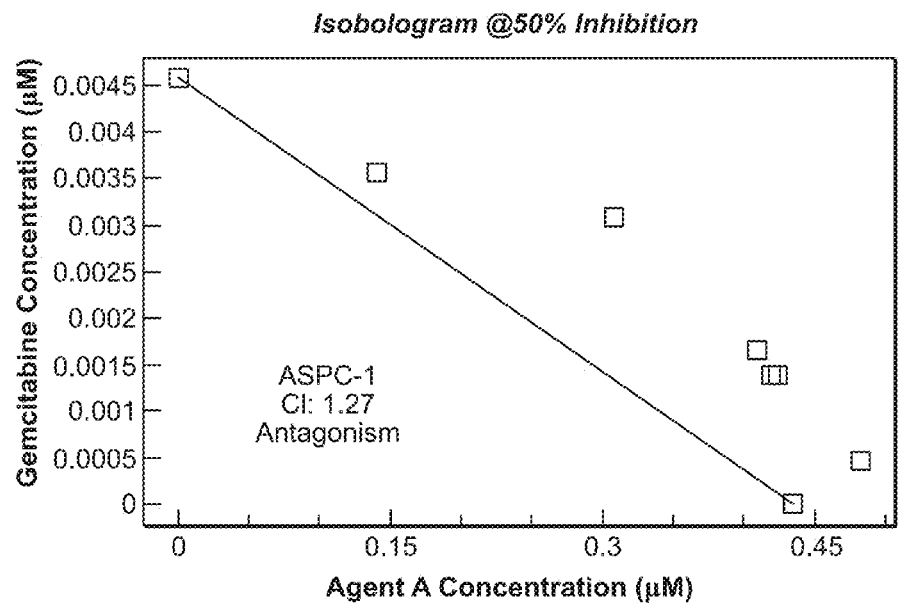
Figure 7C:
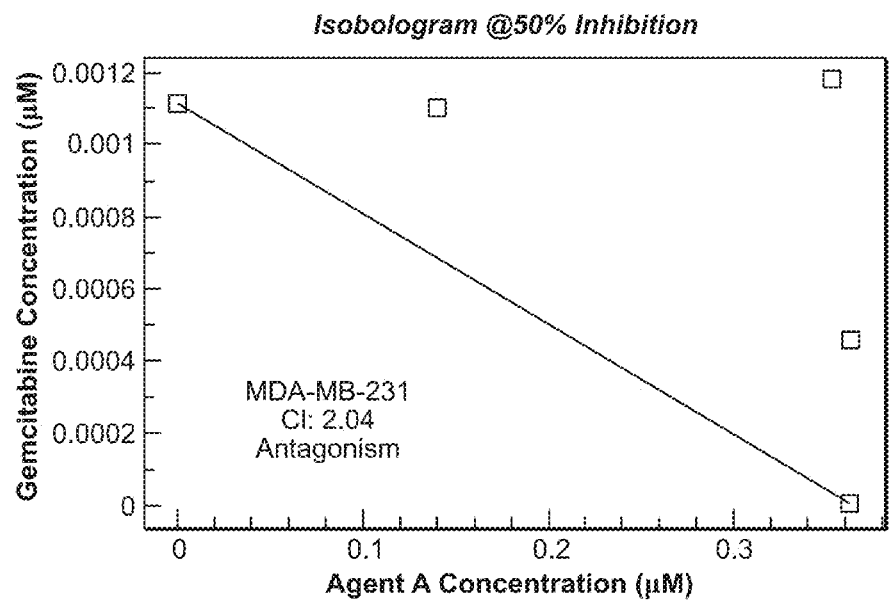
Figure 7D:
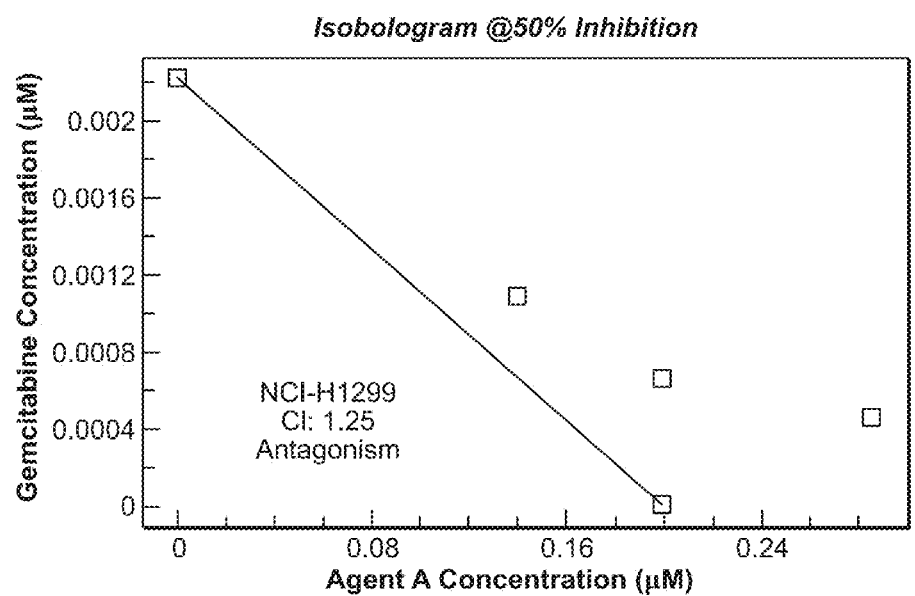

The present invention provides methods of treating a cell proliferative disorder, the method comprising administering to a subject in need thereof a therapeutically effective amount of a compound of formula III, IIIa, IVa, IVb, Va, or Vb, or a pharmaceutically acceptable salt thereof, or a prodrug or metabolite thereof, with one or more pharmaceutically acceptable carriers or excipients in combination with a therapeutically effective amount of a second anti-proliferative agent, with one or more pharmaceutically acceptable carriers or excipients, wherein the cell proliferation disorder is treated.

The present invention provides a pharmaceutical composition for treating a cell proliferative disorder, comprising a combination of (a) a therapeutically effective amount of a compound of formula III, IIIa, IVa, IVb, Va, or Vb, or a pharmaceutically acceptable salt thereof, or a prodrug or metabolite thereof in combination with (b) a therapeutically effective amount of a second anti-proliferative agent. One or more pharmaceutically acceptable carriers or excipients is (are) optionally included in the composition.

A second anti-proliferative agent is preferably a second chemotherapeutic agent.

The cell proliferative disorder can be a precancerous condition or cancer. The cell proliferative disorder can be a hematologic tumor or malignancy, or a solid tumor (or tumors). This method of treating cancer includes a reduction in tumor size. Alternatively, or in addition, the cancer is metastatic cancer and this method of treatment includes inhibition of metastatic cancer cell invasion.

The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine, tositumomab (Bexxar); alemtuzumab (Campath); ibritumomab (In-111 Zevalin); gemtuzumab (Mylotarg); eculizumab (Soliris); ibritumomab (Y-90 Zevalin); denosumab or ibritumomab (Zevalin).

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone;

vinorelbine (Navelbine); camptothecin (CPT); irinotecan (Camptosar); topotecan (Hycamtin); amsacrine or lamellarin D (LAM-D).

Exemplary mTOR inhibitors include, but are not limited to, everolimus (Afinitor) or temsirolimus (Torisel); rapamune, ridaforolimus; or AP23573.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl, PDGFRs and c-Kit), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/Abl and Src), AC-220 (targets Flt3), AC-480 (targets all HER proteins, "pan-HER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, eril/easudil hydrochloride; Rapamune (targets mTOR/FRAP1); Deforolimus (targets mTOR); Certican/Everolimus (targets mTOR/FRAP1); AP23573 (targets mTOR/FRAP1); Eril/Fasudil hydrochloride (targets RHO); Flavopiridol (targets CDK); Seliciclib/CYC202/Roscovitrine (targets CDKs); SNS-032/BMS-387032 (targets CDKs); Ruboxistaurin (targets PKC); Pkc412 (targets PKC); Bryostatin (targets PKC); KAI-9803 (targets PKC); SF1126 (targets PI3K); VX-680 (targets Aurora kinase); Azd1152 (targets Aurora kinase); Any-142886/AZD-6244 (targets MAP/MEK); SCIO-469 (targets MAP/MEK); GW681323 (targets MAP/MEK); CC-401 (targets JNK); CEP-1347 (targets JNK); and PD 332991 (targets CDKs).

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary aromatase inhibitors include, but are not limited to, aminoglutethimide, testolactone (Teslac), anastrozole (Arimidex), Letrozole (Femara), exemestane (Aromasin), Vorozole (Rivizor), Formestane (Lentaron), Fadrozole (Afema), 4-androstene-3,6,17-trione (6-OXO), 1,4,6-androstatrien-3,17-dione (ATD), and 4-hydroxyandrostenedione.

Exemplary anthracyclines include, but are not limited to, daunorubicin (Daunomycin), doxorubicin (Adriamycin), epirubicin, idarubicin, and valrubicin.

Exemplary cytidine analogs include, but are not limited to, gemcitabine, azacytidine (e.g., 5-azacytidine), and cytosine arabinoside (cytarabin, araC, Cytosar).

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxel.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or statins (e.g., lovastatin, atorvastatin, cerivastatin, fluvastatin, mevastatin, pitavastatin, pravastatin, rosuvastatin, and simvastatin).

The present invention also provides a method of treating a cell proliferative disorder, the method comprising administering to a subject a therapeutically effective amount of a compound of formula III, IIIa, IVa, IVb, Va, or Vb, or a pharmaceutically acceptable salt thereof, or a prodrug or metabolite thereof, in combination with a therapeutically effective amount of a second anti-proliferative agent, wherein the compound of formula III, IIIa, IVa, IVb, Va, or Vb, or a pharmaceutically acceptable salt thereof, or a prodrug or metabolite thereof, and the second anti-proliferative agent are not administered concurrently.

In certain preferred embodiments, the compound of formula III, IIIa, IVa, IVb, Va, or Vb is (−)-trans-3-(5,6-dihydro-4H-pyrrolo[3,2,1-ij]quinolin-1-yl)-4-(1H-indol-3-yl)pyrrolidine-2,5-dione.

In certain preferred embodiments, the second anti-proliferative agent is a cytidine analog including, but not limited to, gemcitabine, azacytidine (e.g., 5-azacytidine), and cytosine arabinoside (cytarabin, araC, Cytosar). Preferably, the cytidine analog is gemcitabine.

In another embodiment, the second anti-proliferative agent is an inhibitor of the G1/S phase of the cell cycle.

In certain preferred embodiments, the compound of formula III, IIIa, IVa, IVb, Va, or Vb, or a pharmaceutically acceptable salt thereof, or a prodrug or metabolite thereof, is administered after the administration of the second anti-proliferative agent.

In one embodiment, the compound of formula III, IIIa, IVa, IVb, Va, or Vb, or a pharmaceutically acceptable salt thereof, or a prodrug or metabolite thereof, is administered in a single dose, for 12 hours, 24 hours, 36 hours, 48 hours, 60 hours, 72 hours, 4 days, 5 days, 6 days, 7 days, 10 days, 2 weeks, 3 weeks, or 4 weeks after the administration of the second anti-proliferative agent.

Preferably, the second anti-proliferative agent is administered for no more than 12 or 24 hours and the compound of formula III, IIIa, IVa, IVb, Va, or Vb, or a pharmaceutically acceptable salt thereof, or a prodrug or metabolite thereof, is administered 24 hours after the administration of the second anti-proliferative agent. Most preferably, no drug is administered for at least 12 hours or at least 24 hours prior to the administration of the second anti-proliferative agent.

More preferably, the compound of formula III, IIIa, IVa, IVb, Va, or Vb, or a pharmaceutically acceptable salt thereof, or a prodrug or metabolite thereof, is administered 24 hours after the concentration, or the amount, of the second anti-proliferative agent in the subject is less than 90%, 80%, 70%, 60%, 50%, 40%, 30%, 20% or 10% of its starting concentration, or starting amount, when the compound or agent is administered to the subject. Preferably, the concentration, or amount, of the compound or agent is less than 50% of its starting concentration. More preferably, the concentration, or amount of the compound or agent is less than 10%, 9%, 8%, 7%, 6%, 5%, 4%, 3%, 2%, 1% of its starting concentration, or starting amount.

In one embodiment, the subject is "drug-free" (not administfor the second anti-proliferative agent for 12 hours, 24 hours, 36 hours, 48 hours, 60 hours, 72 hours, 4 days, 5 days, 6 days, 7 days, 10 days, 2 weeks, 3 weeks, or 4 weeks before the compound of formula III, IIIa, IVa, IVb, Va, or Vb, or a pharmaceutically acceptable salt thereof, or a prodrug or metabolite thereof, is administered to the subject. Preferably, the subject is "drug-free" for the second anti-proliferative agent for at least 24 hours, at least 48 hours or at least 72 hours before the compound of formula III, IIIa, IVa, IVb, Va, or Vb, or a pharmaceutically acceptable salt thereof, or a prodrug or metabolite thereof, is administered.

In certain preferred embodiments, the second anti-proliferative agent is administered after the administration of the compound of formula III, IIIa, IVa, IVb, Va, or Vb, or a pharmaceutically acceptable salt thereof, or a prodrug or metabolite thereof.

In one embodiment, the second anti-proliferative agent is administered in a single dose, administered for 30 minutes, 1 hour, 12 hours, 24 hours, 36 hours, 48 hours, 60 hours, 72 hours, 4 days, 5 days, 6 days, 7 days, 10 days, 2 weeks, 3 weeks, or 4 weeks after the administration of the compound of formula III, IIIa, IVa, IVb, Va, or Vb, or a pharmaceutically acceptable salt thereof, or a prodrug or metabolite thereof, to the subject.

Preferably, the compound of formula III, IIIa, IVa, IVb, Va, or Vb, or a pharmaceutically acceptable salt thereof, or a prodrug or metabolite thereof, is administered for at least 24 hours or 48 hours and the second anti-proliferative agent is administered 48 hours after the administration of the compound of formula III, IIIa, IVa, IVb, Va, or Vb, or a pharmaceutically acceptable salt thereof, or a prodrug or metabolite thereof. Most preferably, no drug is administered for at least 12 hours or at least 24 hours prior to the administration of the second anti-proliferative agent.

More preferably, the second anti-proliferative agent is administered 48 hours after the concentration, or the amount, of the compound of formula III, IIIa, IVa, IVb, Va, or Vb, or a pharmaceutically acceptable salt thereof, or a prodrug or metabolite thereof, in the subject is less than 90%, 80%, 70%, 60%, 50%, 40%, 30%, 20% or 10% of its starting concentration, or starting amount, when the compound or agent is administered to the subject. Preferably, the concentration, or amount, of the compound or agent is less than 50% of its starting concentration. More preferably, the concentration, or amount of the compound or agent is less than 10%, 9%, 8%, 7%, 6%, 5%, 4%, 3%, 2%, 1% of its starting concentration, or starting amount.

In one embodiment, the subject is "drug-free" for the compound of formula III, IIIa, IVa, IVb, Va, or Vb, or a pharmaceutically acceptable salt thereof, or a prodrug or metabolite thereof, for 12 hours, 24 hours, 36 hours, 48 hours, 60 hours, 72 hours, 4 days, 5 days, 6 days, 7 days, 10 days, 2 weeks, 3 weeks, or 4 weeks before the second anti-proliferative agent is administered to the subject. Preferably, the subject is "drug-free" for the compound of formula III, IIIa, IVa, IVb, Va, or Vb, or a pharmaceutically acceptable salt thereof, or a prodrug or metabolite thereof, for at least 24 hours, at least 48 hours or at least 72 hours before the second anti-proliferative agent is administered.

As used herein, "drug-free" means that no drug is administered to a subject. It can also mean that a subject does not receive any drug. Preferably, drug-free means that the subject is not administered any anti-proliferative or anti-cancer agent.

Preferred combinatorial therapies include, but are not limited to, (−)-trans-3-(5,6-dihydro-4H-pyrrolo[3,2,1-ij]quinolin-1-yl)-4-(1H-indol-3-yl)pyrrolidine-2,5-dione administered in combination with gemcitabine. In certain embodiments, a subject or patient receives gemcitabine, administered at about 2500 mg/m$^2$ to about 50 mg/m$^2$, once daily. In certain embodiments, gemcitabine is administered at a decreased dose to reduce toxicity. For example, gemcitabine is administered at 1000 mg/m$^2$, 750 mg/m$^2$, 500 mg/m$^2$, 250 mg/m$^2$, 100 mg/m$^2$, or 50 mg/m$^2$ once daily. In certain embodiments, a subject or patient receives (−)-trans-3-(5,6-dihydro-4H-pyrrolo[3,2,1-ij]quinolin-1-yl)-4-(1H-indol-3-yl)pyrrolidine-2,5-dione at 360 mg twice daily. Preferred dosage forms for (−)-trans-3-(5,6-dihydro-4H-pyrrolo[3,2,1-ij]quinolin-1-yl)-4-(1H-indol-3-yl)pyrrolidine-2,5-dione include, but are not limited to, a capsule and a tablet.

The present examples demonstrate a synergistic or, at least an additive, anti-proliferative effect for various cancers, in vitro and in vivo, when (−)-trans-3-(5,6-dihydro-4H-pyrrolo[3,2,1-ij]quinolin-1-yl)-4-(1H-indol-3-yl)pyrrolidine-2,5-dione is administered in combination with gemcitabine. These cancers include, but are not limited to, lung cancer, small cell lung cancer, non-small cell lung cancer, colon cancer, breast cancer, pancreatic cancer, prostate cancer, renal cancer, cervical cancer, brain cancer, gastric/stomach cancer, uterine cancer, intestinal cancer, hepatic cancer, chronic myelogenous leukemia, melanoma, ovarian cancer, translocation-associated renal cell carcinoma (RCC), alveolar soft part sarcoma (ASPS), clear cell sarcoma (CCS), and hepatocellular carcinoma. The anti-proliferative effects of these combinational treatments are increased/enhanced in cell proliferative disorders and cancers in which the effected cells constitutively express or over-express c-Met.

(−)-trans-3-(5,6-dihydro-4H-pyrrolo[3,2,1-ij]quinolin-1-yl)-4-(1H-indol-3-yl)pyrrolidine-2,5-dione is a non-ATP competitive small molecule that selectively targets the c-Met receptor tyrosine kinase. Exposure of c-Met expressing cancer cell lines to (−)-trans-3-(5,6-dihydro-4H-pyrrolo[3,2,1-ij]quinolin-1-yl)-4-(1H-indol-3-yl)pyrrolidine-2,5-dione results in a decrease in phospho-c-Met levels with eventual apoptotic cell death. (−)-trans-3-(5,6-dihydro-4H-pyrrolo[3,2,1-ij]quinolin-1-yl)-4-(1H-indol-3-yl)pyrrolidine-2,5-dione also inhibited the growth of human tumors in multiple mouse xenograft efficacy studies (Munshi N, et al. "ARQ 197, a Novel and Selective Inhibitor of the Human c-Met receptor Tyrosine Kinase with Antitumor Activity". *Mol Cancer Ther* (2010 May 18)).

Gemcitabine is an anti-cancer chemotherapy drug and is used to treat pancreatic cancer, non-small cell lung cancer, bladder cancer, soft-tissue sarcoma and metastatic breast cancer. Gemcitabine is classified as an antimetabolite. The triphosphate analogue of gemcitabine replaces cytidine during DNA replication resulting inhibition of DNA synthesis and induction of apoptosis. The diphosphate analogue of gemcitabine inactivates ribonucleotide reductase enzyme (RNR) and inhibits the production of the deoxyribonucleotides required for DNA replication and repair, and cell apoptosis is induced. Gemcitabine has been shown to arrest cancer cells in G1/S phase (Cerqueira, P. A. Fernandes, M. J. Ramos (2007). "Understanding ribonucleotide reductase inactivation by gemcitabine". *Chemistry, a European Journal* 13 (30): 8507-15).

A compound of formula III, IIIa, IVa, IVb, Va, or Vb of the present invention, or a pharmaceutically acceptable salt, prodrug, metabolite, analog or derivative thereof, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect, a compound of formula III, IIIa, IVa, IVb, Va, or Vb, or a pharmaceutically acceptable salt, prodrug, metabolite, analog or derivative thereof, is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of formula III, IIIa, IVa, IVb, Va, or Vb, or a pharmaceutically acceptable salt, prodrug, metabolite, analog or derivative thereof, (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi's sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. In one aspect, a cell proliferative disorder of the hematologic system includes lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. In another aspect, a cell proliferative disorder of the hematologic system includes hyperplasia, dysplasia, and metaplasia of cells of the hematologic system. In a preferred aspect, compositions of the present invention may be used to treat a cancer selected from the group consisting of a hematologic cancer of the present invention or a hematologic cell proliferative disorder of the present invention. In one aspect, a hematologic cancer of the present invention includes multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. In one aspect, cell proliferative disorders of the lung include all forms of cell proliferative disorders affecting lung cells. In one aspect, cell proliferative disorders of the lung include lung cancer, a precancer or precancerous condition of the lung, benign growths or lesions of the lung, and malignant growths or lesions of the lung, and metastatic lesions in tissue and organs in the body other than the lung. In a preferred aspect, compositions of the present invention may be used to treat lung cancer or cell proliferative disorders of the lung. In one aspect, lung cancer includes all forms of cancer of the lung. In another aspect, lung cancer includes malignant lung neoplasms, carcinoma in situ, typical carcinoid tumors, and atypical carcinoid tumors. In another aspect, lung cancer includes small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. In another aspect, lung cancer includes "scar carcinoma," bronchioalveolar carcinoma, giant cell carcinoma, spindle cell carcinoma, and large cell neuroendocrine carcinoma. In another aspect, lung cancer includes lung neoplasms having histologic and ultrastructual heterogeneity (e.g., mixed cell types).

In one aspect, cell proliferative disorders of the lung include all forms of cell proliferative disorders affecting lung cells. In one aspect, cell proliferative disorders of the lung include lung cancer, precancerous conditions of the lung. In one aspect, cell proliferative disorders of the lung include hyperplasia, metaplasia, and dysplasia of the lung. In another aspect, cell proliferative disorders of the lung include asbestos-induced hyperplasia, squamous metaplasia, and benign reactive mesothelial metaplasia. In another aspect, cell proliferative disorders of the lung include replacement of columnar epithelium with stratified squamous epithelium, and mucosal dysplasia. In another aspect, individuals exposed to inhaled injurious environmental agents such as cigarette smoke and asbestos may be at increased risk for developing cell proliferative disorders of the lung. In another aspect, prior lung diseases that may predispose individuals to development of cell proliferative disorders of the lung include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In a preferred aspect, the cell proliferative disorder of the colon is colon cancer. In a preferred aspect, compositions of the present invention may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, cell proliferative disorders of the colon include all forms of cell proliferative disorders affecting colon cells. In one aspect, cell proliferative disorders of the colon include colon cancer, precancerous conditions of the colon, adenomatous polyps of the colon and metachronous lesions of the colon. In one aspect, a cell proliferative disorder of the colon includes adenoma. In one aspect, cell proliferative disorders of the colon are characterized by hyperplasia, metaplasia, and dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "cell proliferative disorder of the prostate" is a cell proliferative disorder involving cells of the prostate. In one aspect, cell proliferative disorders of the prostate include all forms of cell proliferative disorders affecting prostate cells. In one aspect, cell proliferative disorders of the prostate include prostate cancer, a precancer or precancerous condition of the prostate, benign growths or lesions of the prostate, and malignant growths or lesions of the prostate, and metastatic lesions in tissue and organs in the body other than the prostate. In another aspect, cell proliferative disorders of the prostate include hyperplasia, metaplasia, and dysplasia of the prostate.

A "cell proliferative disorder of the skin" is a cell proliferative disorder involving cells of the skin. In one aspect, cell proliferative disorders of the skin include all forms of cell proliferative disorders affecting skin cells. In one aspect, cell proliferative disorders of the skin include a precancer or precancerous condition of the skin, benign growths or lesions of the skin, melanoma, malignant melanoma and other malignant growths or lesions of the skin, and metastatic lesions in tissue and organs in the body other than the skin. In another aspect, cell proliferative disorders of the skin include hyperplasia, metaplasia, psoriasis, and dysplasia of the skin.

A "cell proliferative disorder of the ovary" is a cell proliferative disorder involving cells of the ovary. In one aspect, cell proliferative disorders of the ovary include all forms of cell proliferative disorders affecting cells of the ovary. In one aspect, cell proliferative disorders of the ovary include a precancer or precancerous condition of the ovary, benign growths or lesions of the ovary, ovarian cancer, malignant growths or lesions of the ovary, and metastatic lesions in tissue and organs in the body other than the ovary. In another aspect, cell proliferative disorders of the ovary include hyperplasia, metaplasia, and dysplasia of cells of the ovary.

A "cell proliferative disorder of the breast" is a cell proliferative disorder involving cells of the breast. In one aspect, cell proliferative disorders of the breast include all forms of cell proliferative disorders affecting breast cells. In one aspect, cell proliferative disorders of the breast include breast cancer, a precancer or precancerous condition of the breast, benign growths or lesions of the breast, and malignant growths or lesions of the breast, and metastatic lesions in tissue and organs in the body other than the breast. In another aspect, cell proliferative disorders of the breast include hyperplasia, metaplasia, and dysplasia of the breast.

In one aspect, a cell proliferative disorder of the breast is a precancerous condition of the breast. In one aspect, compositions of the present invention may be used to treat a precancerous condition of the breast. In one aspect, a precancerous condition of the breast includes atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). In another aspect, a precancerous condition of the breast has been staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

In a preferred aspect, the cell proliferative disorder of the breast is breast cancer. In a preferred aspect, compositions of the present invention may be used to treat breast cancer. In one aspect, breast cancer includes all forms of cancer of the breast. In one aspect, breast cancer includes primary epithelial breast cancers. In another aspect, breast cancer includes cancers in which the breast is involved by other tumors such as lymphoma, sarcoma or melanoma. In another aspect, breast cancer includes carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. In one aspect, breast cancer includes Stage I, II, IIIA, IIIB, IIIC and IV breast cancer. In one aspect, ductal carcinoma of the breast includes invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. In one aspect, lobular carcinoma of the breast includes invasive lobular carcinoma with predominant in situ component, invasive lobular carcinoma, and infiltrating lobular carcinoma. In one aspect, breast cancer includes Paget's disease, Paget's disease with intraductal carcinoma, and Paget's disease with invasive ductal carcinoma. In another aspect, breast cancer includes breast neoplasms having histologic and ultrastructual heterogeneity (e.g., mixed cell types).

In a preferred aspect, a compound of formula III, IIIa, IVa, IVb, Va, or Vb may be used to treat breast cancer. In one aspect, a breast cancer that is to be treated includes familial breast cancer. In another aspect, a breast cancer that is to be treated includes sporadic breast cancer. In one aspect, a breast cancer that is to be treated has arisen in a male subject. In one aspect, a breast cancer that is to be treated has arisen in a female subject. In one aspect, a breast cancer that is to be treated has arisen in a premenopausal female subject or a postmenopausal female subject. In one aspect, a breast cancer that is to be treated has arisen in a subject equal to or older than 30 years old, or a subject younger than 30 years old. In one aspect, a breast cancer that is to be treated has arisen in a subject equal to or older than 50 years old, or a subject younger than 50 years old. In one aspect, a breast cancer that is to be treated has arisen in a subject equal to or older than 70 years old, or a subject younger than 70 years old.

In one aspect, a breast cancer that is to be treated has been typed to identify a familial or spontaneous mutation in BRCA1, BRCA2, or p53. In one aspect, a breast cancer that is to be treated has been typed as having a HER2/neu gene amplification, as overexpressing HER2/neu, or as having a low, intermediate or high level of HER2/neu expression. In another aspect, a breast cancer that is to be treated has been typed for a marker selected from the group consisting of estrogen receptor (ER), progesterone receptor (PR), human epidermal growth factor receptor-2, Ki-67, CA15-3, CA 27-29, and c-Met. In one aspect, a breast cancer that is to be treated has been typed as ER-unknown, ER-rich or ER-poor. In another aspect, a breast cancer that is to be treated has been typed as ER-negative or ER-positive. ER-typing of a breast cancer may be performed by any reproducible means. In a preferred aspect, ER-typing of a breast cancer may be performed as set forth in Onkologie 27: 175-179 (2004). In one aspect, a breast cancer that is to be treated has been typed as PR-unknown, PR-rich or PR-poor. In another aspect, a breast cancer that is to be treated has been typed as PR-negative or PR-positive. In another aspect, a breast cancer that is to be treated has been typed as receptor positive or receptor negative. In one aspect, a breast cancer that is to be treated has been typed as being associated with elevated blood levels of CA 15-3, or CA 27-29, or both.

In one aspect, a breast cancer that is to be treated includes a localized tumor of the breast. In one aspect, a breast cancer that is to be treated includes a tumor of the breast that is associated with a negative sentinel lymph node (SLN) biopsy. In one aspect, a breast cancer that is to be treated includes a tumor of the breast that is associated with a positive sentinel lymph node (SLN) biopsy. In another aspect, a breast cancer that is to be treated includes a tumor of the breast that is associated with one or more positive auxiliary lymph nodes, where the auxiliary lymph nodes have been staged by any applicable method. In another aspect, a breast cancer that is to be treated includes a tumor of the breast that has been typed as having nodal negative status (e.g., node-negative) or nodal positive status (e.g., node-positive). In another aspect, a breast cancer that is to be treated includes a tumor of the breast that has metastasized to other locations in the body. In one aspect, a breast cancer that is to be treated is classified as having metastasized to a location selected from the group consisting of bone, lung, liver, or brain. In another aspect a breast cancer that is to be treated is classified according to a characteristic selected from the group consisting of metastatic, localized, regional, local-regional, locally advanced, distant, multicentric, bilateral, ipsilateral, contralateral, newly diagnosed, recurrent, and inoperable.

In one aspect, a compound of formula III, IIIa, IVa, IVb, Va, or Vb may be used to treat or prevent a cell proliferative disorder of the breast, or to treat or prevent breast cancer, in a subject having an increased risk of developing breast cancer relative to the population at large. In one aspect, a subject with an increased risk of developing breast cancer relative to the population at large is a female subject with a family history or personal history of breast cancer. In another aspect, a subject with an increased risk of developing breast cancer relative to the population at large is a female subject having a germ-line or spontaneous mutation in BRCA1 or BRCA2, or both. In one aspect, a subject with an increased risk of developing breast cancer relative to the population at large is a female subject with a family history of breast cancer and a germ-line or spontaneous mutation in BRCA1 or BRCA2, or both. In another aspect, a subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. In one aspect, a subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

In another aspect, a breast cancer that is to be treated has been histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. In another aspect, a breast cancer that is to be treated has been assigned a tumor grade according to the International Consensus Panel on the Treatment of Breast Cancer selected from the group consisting of grade 1, grade 1-2, grade 2, grade 2-3, or grade 3.

In one aspect, a cancer that is to be treated has been staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) has been assigned a stage of MX, M0, or M1. In another aspect, a cancer that is to be treated has been staged according to an American Joint Committee on Cancer (AJCC) classification as Stage I, Stage IIA, Stage IIB, Stage IIIA, Stage IIIB, Stage IIIC, or Stage IV. In another aspect, a cancer that is to be treated has been assigned a grade according to an AJCC classification as Grade GX (e.g., grade cannot be assessed), Grade 1, Grade 2, Grade 3 or Grade 4. In another aspect, a cancer that is to be treated has been staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

In one aspect, a cancer that is to be treated includes a tumor that has been determined to be less than or equal to about 2 centimeters in diameter. In another aspect, a cancer that is to be treated includes a tumor that has been determined to be from about 2 to about 5 centimeters in diameter. In another aspect, a cancer that is to be treated includes a tumor that has been determined to be greater than or equal to about 3 centimeters in diameter. In another aspect, a cancer that is to be treated includes a tumor that has been determined to be greater than 5 centimeters in diameter. In another aspect, a cancer that is to be treated is classified by microscopic appearance as well differentiated, moderately differentiated, poorly differentiated, or undifferentiated. In another aspect, a cancer that is to be treated is classified by microscopic appearance with respect to mitosis count (e.g., amount of cell division) or nuclear pleiomorphism (e.g., change in cells). In another aspect, a cancer that is to be treated is classified by microscopic appearance as being associated with areas of necrosis (e.g., areas of dying or degenerating cells). In one aspect, a cancer that is to be treated is classified as having an abnormal karyotype, having an abnormal number of chromosomes, or having one or more chromosomes that are abnormal in appearance. In one aspect, a cancer that is to be treated is classified as being aneuploid, triploid, tetraploid, or as having an altered ploidy. In one aspect, a cancer that is to be treated is classified as having a chromosomal translocation, or a deletion or duplication of an entire chromosome, or a region of deletion, duplication or amplification of a portion of a chromosome.

In one aspect, a cancer that is to be treated is evaluated by DNA cytometry, flow cytometry, or image cytometry. In one aspect, a cancer that is to be treated has been typed as having 10%, 20%, 30%, 40%, 50%, 60%, 70%, 80%, or 90% of cells in the synthesis stage of cell division (e.g., in S phase of cell division). In one aspect, a cancer that is to be treated has been typed as having a low S-phase fraction or a high S-phase fraction.

As used herein, a "normal cell" is a cell that cannot be classified as part of a "cell proliferative disorder." In one aspect, a normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of formula III, IIIa, IVa, IVb, Va, or Vb that has been or will be tested in one or more in vitro or in vivo biological assays, in order to determine if that compound is likely to elicit a desired biological or medical response in a cell, tissue, system, animal or human that is being sought by a researcher or clinician. In one aspect, a candidate compound is a compound of formula III or IIIa; in another aspect, a candidate compound is a compound of formula IVa, IVb, Va, or Vb. In a preferred aspect, the biological or medical response is treatment of cancer. In another aspect, the biological or medical response is treatment or prevention of a cell proliferative disorder. In one aspect, in vitro or in vivo biological assays include, but are not limited to, enzymatic activity assays, electrophoretic mobility shift assays, reporter gene assays, in vitro cell viability assays, and the assays.

As used herein, "monotherapy" refers to administration of a single active or therapeutic compound to a subject in need thereof. Preferably, monotherapy will involve administration of a therapeutically effective amount of an active compound. For example, cancer monotherapy with (±)-cis-3-(5,6-dihydro-4H-pyrrolo[3,2,1-ij]quinolin-1-yl)-4-(1H-indol-3-yl)pyrrolidine-2,5-dione comprises administration of a therapeutically effective amount of (±)-cis-3-(5,6-dihydro-4H-pyrrolo[3,2,1-ij]quinolin-1-yl)-4-(1H-indol-3-yl)pyrrolidine-2,5-dione, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of formula III, IIIa, IVa, IVb, Va, or Vb is more effective than combination therapy in inducing a desired biological effect. Monotherapeutic effectiveness of the compounds of formula III, IIIa, IVa, IVb, Va, or Vb is shown in PCT Publication No. WO 2006/086484.

As used herein, "treating" describes the management and care of a patient for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving monotherapy with a drug that is not a compound of formula III, IIIa, IVa, IVb, Va, or Vb, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of formula III, IIIa, IVa, IVb, Va, or Vb, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

As used herein, the term "selectively" means tending to occur at a higher frequency in one population than in another population. In one aspect, the compared populations are cell populations. In a preferred aspect, a compound of formula III, IIIa, IVa, IVb, Va, or Vb, or a pharmaceutically acceptable salt, prodrug, metabolite, analog or derivative thereof, acts selectively on a cancer or precancerous cell but not on a normal cell. In another preferred aspect, a compound of formula III, IIIa, IVa, IVb, Va, or Vb, or a pharmaceutically acceptable salt, prodrug, metabolite, analog or derivative thereof, acts selectively to modulate one molecular target (e.g., c-Met) but does not significantly modulate another molecular target (e.g., Protein Kinase C). In another preferred aspect, the invention provides a method for selectively inhibiting the activity of an enzyme, such as a kinase. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

In a preferred aspect, a compound of formula III, IIIa, IVa, IVb, Va, or Vb or a pharmaceutically acceptable salt, prodrug, metabolite, analog or derivative thereof, modulates the activity of a molecular target (e.g., c-Met). In one aspect, modulating refers to stimulating or inhibiting an activity of a molecular target. Preferably, a compound of formula III, IIIa, IVa, IVb, Va, or Vb modulates the activity of a molecular target if it stimulates or inhibits the activity of the molecular target by at least 2-fold relative to the activity of the molecular target under the same conditions but lacking only the presence of said compound. More preferably, a compound of formula III, IIIa, IVa, IVb, Va, or Vb modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In one aspect, a compound of formula III, IIIa, IVa, IVb, Va, or Vb, or a pharmaceutically acceptable salt, prodrug, metabolite, analog or derivative thereof, does not significantly modulate the activity of a molecular target if the addition of the compound does not stimulate or inhibit the activity of the molecular target by greater than 10% relative to the activity of the molecular target under the same conditions but lacking only the presence of said compound. In a preferred aspect, a compound of formula III, IIIa, IVa, IVb, Va, or Vb does not significantly modulate the activity of Protein Kinase C.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of formula III, IIIa, IVa, IVb, Va, or Vb demonstrates a minimum of a four fold differential, preferably a ten fold differential, more preferably a fifty fold differential, in the dosage required to achieve a biological effect. Preferably, a compound of formula III, IIIa, IVa, IVb, Va, or Vb demonstrates this differential across the range of inhibition, and the differential is exemplified at the $IC_{50}$, i.e., a 50% inhibition, for a molecular target of interest.

In a preferred embodiment, administering a compound of formula III, IIIa, IVa, IVb, Va, or Vb, or a pharmaceutically acceptable salt, prodrug, metabolite, analog or derivative thereof, to a cell or a subject in need thereof results in modulation (i.e., stimulation or inhibition) of an activity of c-Met. As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK. c-Met knockdown has been shown to inhibit cancer cell growth in a cell-type-specific manner. MDA-MB-231, NCI-H661, NCI-H441, MIA PaCa-2, HT29 and MKN-45 human cancer cells. c-Met knockdown induces caspase-dependent apoptosis in a cell type-specific manner. Thus, the present invention is directed to the treatment of cell proliferative disorders where the cells express c-Met at high levels or express active c-Met.

In a preferred embodiment, administering a compound of formula III, IIIa, IVa, IVb, Va, or Vb, or a pharmaceutically acceptable salt, prodrug, metabolite, analog or derivative thereof, to a cell or a subject in need thereof results in modulation (i.e., stimulation or inhibition) of an activity of ERK 1 or ERK 2, or both. As used herein, an activity of ERK 1 or ERK 2 refers to any biological function or activity that is carried out by ERK 1 or ERK 2. For example, a function of ERK 1 or ERK 2 includes phosphorylation of downstream target proteins.

In one aspect, activating refers to placing a composition of matter (e.g., protein or nucleic acid) in a state suitable for carrying out a desired biological function. In one aspect, a composition of matter capable of being activated also has an unactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. In one aspect, a cell cycle checkpoint regulator is a protein. In another aspect, a cell cycle checkpoint regulator is not a protein.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) *Proc Natl Acad Sci USA*. 100(5): 2674-8. In an aspect, cell death occurs by apoptosis.

In a preferred aspect, an effective amount of a compound of formula III, IIIa, IVa, IVb, Va, or Vb, or a pharmaceutically acceptable salt, prodrug, metabolite, analog or derivative thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

In one aspect, contacting a cell with a compound of formula III, IIIa, IVa, IVb, Va, or Vb, or a pharmaceutically acceptable salt, prodrug, metabolite, analog or derivative thereof, induces or activates cell death selectively in cancer cells. Preferably, administering to a subject in need thereof a compound of formula III, IIIa, IVa, IVb, Va, or Vb, or a pharmaceutically acceptable salt, prodrug, metabolite, analog or derivative thereof, induces or activates cell death selectively in cancer cells. In another aspect, contacting a cell with a compound of formula III, IIIa, IVa, IVb, Va, or Vb, or a pharmaceutically acceptable salt, prodrug, metabolite, analog or derivative thereof, induces cell death selectively in one or more cells affected by a cell proliferative disorder. Preferably, administering to a subject in need thereof a compound of formula III, IIIa, IVa, IVb, Va, or Vb, or a pharmaceutically acceptable salt, prodrug, metabolite, analog or derivative thereof, induces cell death selectively in one or more cells affected by a cell proliferative disorder. In a preferred aspect, the present invention relates to a method of treating or preventing cancer by administering a compound of formula III, IIIa, IVa, IVb, Va, or Vb, or a pharmaceutically acceptable salt, prodrug, metabolite, analog or derivative thereof to a subject in need thereof, where administration of the compound of formula III, IIIa, IVa, IVb, Va, or Vb, or a pharmaceutically acceptable salt, prodrug, metabolite, analog or derivative thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Amusable et al., *Current Protocols in Molecular Biology*, John Wiley and Sons, Inc. (2005); Sam brook et al., *Molecular Cloning, A Laboratory Manual* (3d ed.), Cold Spring Harbor Press, Cold Spring Harbor, N.Y. (2000); Collagen et al., *Current Protocols in Immunology*, John Wiley & Sons, N.Y.; Anna et al., *Current Protocols in Pharmacology*, John Wiley & Sons, N.Y.; Final et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

2. Pyrroloquinolinyl-pyrrole-2,5-diones and pyrroloquinolinyl-pyrrolidine-2,5-diones The pyrroloquinolinyl-pyrrole-2,5-dione compounds of formula III and IIIa are:

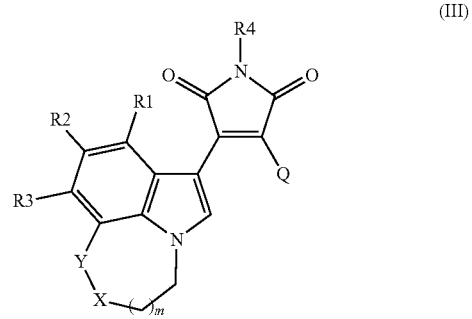

(III)

where:
R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—(C₁-C₆) substituted alkyl, —O—(C₃-C₉) cycloalkyl, and —O—(C₃-C₉) substituted cycloalkyl, aryl, heteroaryl, heterocyclyl;

R4 is independently selected from the group consisting of hydrogen, —(C₁-C₆) alkyl, —CH₂R7;

R5, R6 are independently selected from the group consisting of hydrogen, and —(C₁-C₆) alkyl;

R7 is independently selected from the group consisting of —O—P(=O)(OH)₂, —O—P(=O)(—OH)(—O—(C₁-C₆) alkyl), —O—P(=O)(—O—(C₁-C₆) alkyl)₂, —O—P(=O)(—OH) (—O—(CH₂)-phenyl), —O—P(=O)(—O—(CH₂)-phenyl)₂, a carboxylic acid group, an amino carboxylic acid group and a peptide;

Q is selected from the group consisting of aryl, heteroaryl, -Ovary, -Snarly, —O heteroaryl, and —S heteroaryl;

X is selected from the group consisting of —(CH₂)—, —(NR8)-, S, and O;

R8 is independently selected from the group consisting of hydrogen, —(C₁-C₆) alkyl, —(C₁-C₆) substituted alkyl, —(C₃-C₉) cycloalkyl, —(C₃-C₉) substituted cycloalkyl, and —O—(C₁-C₆) alkyl, —C(=O)—O—(C₁-C₆) alkyl and —C(=O)—O—(C₁-C₆) substituted alkyl;

Y is selected from the group consisting of —(CH₂)— or a bond;

wherein said aryl, heteroaryl, -Ovary, -Snarly, —O heteroaryl, and —S heteroaryl groups may be substituted with one or more substituents independently selected from the group consisting of F, Cl, Br, I, —NR5R6, —(C₁-C₆) alkyl, —(C₁-C₆) substituted alkyl, —(C₃-C₉) cycloalkyl, —(C₃-C₉) substituted cycloalkyl, —O—(C₁-C₆) alkyl, —O—(C₁-C₆) substituted alkyl, —O—(C₃-C₉) cycloalkyl, —O—(C₃-C₉) substituted cycloalkyl, -aryl, -aryl-(C₁-C₆) alkyl, -aryl-(C₁-C₆) alkyl, -Ovary, —O—(C₁-C₄) alkyl aryl, heteroaryl, heterocyclyl, —O—(C₁-C₄) alkyl heterocycle, and —(S(=O)₂)—(C₁-C₆) alkyl; and m is 1 or 2.

For the compound of formula IIIa, Q is selected from the group consisting of aryl, heteroaryl, -Ovary, -Snarly, —O heteroaryl, and —S heteroaryl, provided that when R4 is hydrogen, or (C₁-C₄) alkyl, Q is not 3-indolyl or substituted 3-indolyl.

The pyrroloquinolinyl-pyrrolidine-2,5-dione compounds of formula IVa, IVb, Va, or Vb, are:

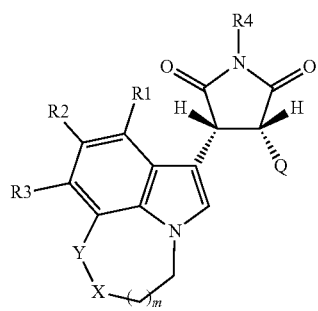

(IVa)

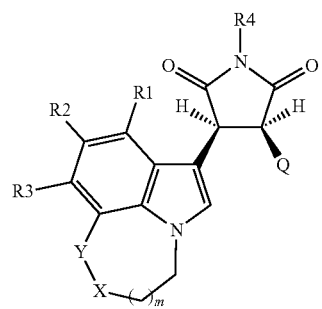

(IVb)

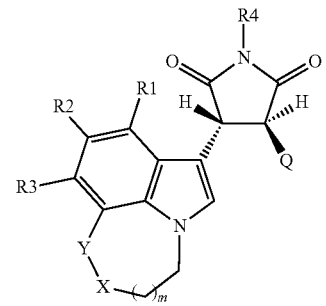

(Va)

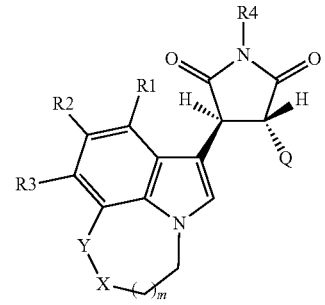

(Vb)

where:

R1, R2 and R3 are independently selected from the group consisting of hydrogen, F, Cl, Br, I, —NR5R6, —(C₁-C₆) alkyl, —(C₁-C₆) substituted alkyl, —(C₃-C₉) cycloalkyl, —(C₃-C₉) substituted cycloalkyl, —O—(C₁-C₆) alkyl, —O—(C₁-C₆) substituted alkyl, —O—(C₃-C₉) cycloalkyl, and —O—(C₃-C₉) substituted cycloalkyl, aryl, heteroaryl, heterocyclyl;

R4 is independently selected from the group consisting of hydrogen, —(C₁-C₆) alkyl, —CH₂R7;

R5, R6 are independently selected from the group consisting of hydrogen, and —(C₁-C₆) alkyl;

R7 is independently selected from the group consisting of —O—P(=O)(OH)₂, —O—P(=O)(—OH)(—O—(C₁-C₆) alkyl), —O—P(=O)(—O—(C₁-C₆) alkyl)₂, —O—P(=O) (—OH) (—O—(CH₂)-phenyl), —O—P(=O)(—O—(CH₂)-phenyl)₂, a carboxylic acid group, an amino carboxylic acid group and a peptide;

Q is selected from the group consisting of aryl, heteroaryl, -Ovary, -Snarly, —O heteroaryl, and —S heteroaryl;

X is selected from the group consisting of —(CH₂)—, —(NR8)-, S, and O;

R8 is independently selected from the group consisting of hydrogen, —(C₁-C₆) alkyl, —(C₁-C₆) substituted alkyl, —(C₃-C₉) cycloalkyl, —(C₃-C₉) substituted cycloalkyl, and —O—(C₁-C₆) alkyl, —C(=O)—O—(C₁-C₆) alkyl and —C(=O)—O—(C₁-C₆) substituted alkyl;

Y is selected from the group consisting of —(CH$_2$)— or a bond;

wherein said aryl, heteroaryl, -Ovary, -Snarly, —O heteroaryl, and —S heteroaryl groups may be substituted with one or more substituents independently selected from the group consisting of F, Cl, Br, I, —NR5R6, —(C$_1$-C$_6$) alkyl, —(C$_1$-C$_6$) substituted alkyl, —(C$_3$-C$_9$) cycloalkyl, —(C$_3$-C$_9$) substituted cycloalkyl, —O—(C$_1$-C$_6$) alkyl, —O—(C$_1$-C$_6$) substituted alkyl, —O—(C$_3$-C$_9$) cycloalkyl, —O—(C$_3$-C$_9$) substituted cycloalkyl, -aryl, -aryl-(C$_1$-C$_6$) alkyl, -aryl-(C$_1$-C$_6$) alkyl, -Ovary, —O—(C$_1$-C$_4$) alkyl aryl, heteroaryl, heterocyclyl, —O—(C$_1$-C$_4$) alkyl heterocycle, and —(S(=O)$_2$)—(C$_1$-C$_6$) alkyl; and m is 1 or 2.

The preparation of a compound of formula III, IIIa, IVa, IVb, Va or Vb is described in international application PCT/US2010/023893, the entire contents of which are incorporated herein by reference.

2.1. DEFINITIONS

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Acyl groups may be denoted by a range, thus, for example, a (C$_1$-C$_6$) alkyl group is an alkyl group having from one to six carbon atoms in the straight or branched alkyl backbone. Substituted and unsubstituted alkyl groups may independently be (C$_1$-C$_5$) alkyl, (C$_1$-C$_6$) alkyl, (C$_1$-C$_{10}$) alkyl, (C$_3$-C$_{10}$) alkyl, or (C$_5$-C$_{10}$) alkyl. Unless expressly stated, the term "alkyl" does not include "cycloalkyl."

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., (C$_3$-C$_6$) cycloalkyl) is a ring structure having between 3 and 6 carbon atoms in the ring. When no range is given, then cycloalkyl has between three and nine carbon atoms ((C$_3$-C$_9$) cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from three to nine carbon atoms in the ring structure.

The term substituted alkyl and substituted cycloalkyl, refer to alkyl and cycloalkyl groups, as defined above, substituted with one or more substituents independently selected from the group consisting of fluorine, aryl, heteroaryl, —O—(C$_1$-C$_6$) alkyl, and —NR5R6, where R5 and R6 are independently selected from the group consisting of hydrogen and —(C$_1$-C$_6$) alkyl.

The term "aryl" refers to an aromatic carbocyclic group, having one, two, or three aromatic rings. Exemplary aryl groups include, without limitation, phenyl, naphthyl, and the like. Aryl groups include one, two, or three aromatic rings structures fused with one or more additional nonromantic carbocyclic or heterocyclic rings having from 4-9 members. Examples of fused aryl groups include benzocyclobutene, indanyl, tetrahydronapthylenyl, 1,2,3,4-tetrahydrophenanthrenyl, tetrahydroanthracenyl, 1,4-dihydro-1,4-methanonaphthalenyl, benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of heteroatom in the aromatic ring are denoted by the type of hetero atom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazolyl, quinolyl, quinazolinyl, thiazolyl, benzo[b]thiophenyl, furanyl, imidazolyl, indolyl, and the like.

The terms "heterocyclyl" or "heterocycle" refers to either saturated or unsaturated, stable non-aromatic ring structures that may be fused, spiro or bridged to form additional rings. Each heterocycle consists of one or more carbon atoms and from one to four heteroatoms selected from the group consisting of nitrogen, oxygen and sulfur. "Heterocyclyl" or "heterocycle" include stable non-aromatic 3-7 membered monocyclic heterocyclic ring structures and 8-11 membered bicyclic heterocyclic ring structures. A heterocyclyl radical may be attached at any endocyclic carbon or nitrogen atom that results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, piperazinyl, pyranyl, pyrrolidinyl, morpholinyl, thiomorpholinyl, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, dithiolyl, sulfolanyl, dioxanyl, dioxolanyl, tetrahydrofurodihydrofuranyl, tetrahydropyranodihydro-furanyl, dihydropyranyl, tetrahydrofurofuranyl, tetrahydropyranofuran, quinuclidinyl (1-azabicyclo[2.2.2]octanyl) and tropanyl (8-methyl-8-azabicyclo[3.2.1]octanyl).

For the purpose of the Q substituent, the term "substituted 3-indolyl" refers to a 3-indolyl group substituted with one or more substituents selected from the group consisting of: F, Cl, Br, I, —NR5R6, —(C$_1$-C$_6$) alkyl, —(C$_1$-C$_6$) substituted alkyl, —(C$_3$-C$_9$) cycloalkyl, —(C$_3$-C$_9$) substituted cycloalkyl, —O—(C$_1$-C$_6$) alkyl, —O—(C$_1$-C$_6$) substituted alkyl, —O—(C$_3$-C$_9$) cycloalkyl, —O—(C$_3$-C$_9$) substituted cycloalkyl, -aryl, -aryl-(C$_1$-C$_6$) alkyl, -aryl-O—(C$_1$-C$_6$) alkyl, —O-aryl, —O—(C$_1$-C$_4$) alkyl-aryl, heteroaryl, heterocyclyl, —O—(C$_1$-C$_4$) alkyl-heterocycle, and —(S(=O)$_2$)—(C$_1$-C$_6$) alkyl; where R5, R6 are independently selected from the group consisting of hydrogen, and —(C$_1$-C$_6$) alkyl.

For the purposes of the R7 substituent, the term "carboxylic acid group" refers to a group of the form —O—C(=O)—(C$_1$-C$_6$) alkyl, —O—C(=O)—(C$_3$-C$_9$) cycloalkyl, —O—C(=O)-aryl, —O—C(=O)-heteroaryl, —O—C(=O)-heterocycle, —O—C(=O)—(C$_1$-C$_6$) alkyl-aryl, —O—C(=O)—(C$_1$-C$_6$) alkyl-heteroaryl, or —O—C(=O)—(C$_1$-C$_6$) alkyl-heterocycle. Included in "carboxylic acid group" are groups of the form —O—C(=O)—(C$_1$-C$_6$) alkyl, —O—C(=O)—(C$_3$-C$_9$) cycloalkyl, —O—C(=O)-aryl, —O—C(=O)-heteroaryl, —O—C(=O)-heterocycle, —O—C(=O)—(C$_1$-C$_6$) alkyl-aryl, —O—C(=O)—(C$_1$-C$_6$) alkyl-heteroaryl, or —O—C(=O)—(C$_1$-C$_6$) alkyl-heterocycle substituted with one or more substituent independently selected from the group consisting of: F, Cl, Br, I, —OH, —SH, —NR5R6, —(C$_1$-C$_6$) alkyl, —(C$_1$-C$_6$) substituted alkyl, —(C$_3$-C$_9$) cycloalkyl, —(C$_3$-C$_9$) substituted cycloalkyl, —O—(C$_1$-C$_6$) alkyl, —O—(C$_1$-C$_6$) substituted alkyl, —S—(C$_1$-C$_6$) alkyl, —O—(C$_3$-C$_9$) cycloalkyl, —O—(C$_3$-C$_9$) substituted cycloalkyl, -aryl, —O-aryl, —O—(C$_1$-C$_4$) alkyl-aryl, heteroaryl, heterocyclyl, —O—(C$_1$-C$_4$) alkyl-heterocycle, —(S(=O)$_2$)—(C$_1$-C$_6$) alkyl, —NH—C(=NH)—NH$_2$ (i.e., guanido), —COOH, and —C(=O)—NR5R6, where R5 and R6 are independently selected from the group consisting of hydrogen, and —(C$_1$-C$_6$) alkyl. In addition, for the purposes of the R7 substituent the term "amino carboxylic acid group" refers to a carboxylic acid group, including carboxylic acid groups substituted with one or more of the above-stated substituents, which bears one or more independently selected amino groups of the form —NR5R6 where R5 and R6 are independently selected from the group consisting of hydrogen and (C1-C6) alkyl.

In one embodiment of this invention, R7 is an alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof. In another embodiment the of the invention, R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine.

For the purposes of the R7 substituent, the term "peptide" refers to a dipeptide, tripeptide, tetrapeptide or pentapeptide, which release two, three, four, or five amino or imino acids (e.g., proline) respectively upon hydrolysis. For the purpose of R7, peptides are linked to the remainder of the molecule through an ester linkage. In one embodiment, peptides of R7 are comprised of alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof; and in a more preferred version of this embodiment, the carboxyl group involved in the ester linkage is the carboxyl terminal COOH group of the peptide, as opposed to a side chain carboxyl. In another embodiment the of the invention, R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine; and in a more preferred version of this preferred embodiment, the carboxyl group involved in the ester linkage is the carboxyl terminal COOH group of the peptide, as opposed to a side chain carboxyl.

2.2. PREFERRED COMPOUNDS

Included in the preferred embodiments are compounds of formula III, IIIa, IVa, IVb, Va, or Vb, wherein Q is selected from the group consisting of aryl, heteroaryl, —O-aryl, —S-aryl, —O-heteroaryl, and —S-heteroaryl, provided that Q is not 3-indolyl or a substituted 3-indolyl. In other preferred embodiments Q is selected from the group consisting of aryl, heteroaryl, —O-aryl, —S-aryl, —O-heteroaryl, and —S-heteroaryl, provided that when R4 is hydrogen, cycloalkyl, or alkyl, Q is not 3-indolyl or a substituted 3-indolyl. In still other preferred embodiments Q is selected from the group consisting of aryl, heteroaryl, —O-aryl, —S-aryl, —O-heteroaryl, and —S-heteroaryl, provided that when R4 is hydrogen, (C$_3$-C$_4$) cycloalkyl, or (C$_1$-C$_4$) alkyl, Q is not 3-indolyl or substituted 3-indolyl. In another preferred embodiment Q is 3-indolyl or a substituted 3-indolyl provided that R4 is not hydrogen, cycloalkyl, or alkyl. In still another preferred embodiment Q is 3-indolyl or a substituted 3-indolyl provided that R4 is not hydrogen, (C$_3$-C$_4$) cycloalkyl, or (C$_1$-C$_4$) alkyl.

Other preferred embodiments include compounds of formula III, IIIa, IVa, IVb, Va, or Vb where R4 is —CH$_2$R7. These compounds may serve as prodrug forms of the corresponding compounds of formula III, IIIa, IVa, IVb, Va, or Vb where R4 is H. The prodrug form is cleaved by hydrolysis to release the corresponding compound where R4 is H. The hydrolysis may occur by enzymatic or nonenzymatic routes that produce the corresponding hydroxymethylene derivative, which upon subsequent hydrolysis, result in the release of compounds where R4 is H. In one such preferred embodiment R4 is —CH$_2$R7, where R7 is —O—P(=O)(OH)$_2$, —O—P(=O)(—OH)(—O—(C$_1$-C$_6$)alkyl), or —O—P(=O)(—O—(C$_1$-C$_6$)alkyl)$_2$. In one embodiment where R7 is —O—P(=O)(—O—(C$_1$-C$_6$)alkyl)$_2$, the alkyl groups are independently selected. In another preferred embodiment, R4 is —CH$_2$R7, where R7 is a carboxylic acid group or an amino carboxylic acid group. In still another preferred embodiment R7 is a peptide; where in a more preferred embodiment the peptide is linked through an ester bond formed with the carboxyl terminal COOH group of the peptide chain to the remainder of the compound. In other preferred separate and independent embodiments of compounds of formula III, IIIa, IVa, IVb, Va, or Vb where R4 is —CH$_2$R7 and R7 is a peptide, the peptide may be a dipeptide, a tripeptide, a tetrapeptide or a pentapeptide. Preferred amino acid compositions for peptides of the R7 functionality are described above.

Embodiments of compounds of formula III, IIIa, IVa, IVb, Va, or Vb include those where X is selected from the group consisting of —(NR8)-, S, and O, where R8 is independently selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl. Other embodiments of compounds of formula III, IIIa, IVa, IVb, Va, or Vb include those where X is —CH$_2$—. In other embodiments of compounds of formula III, IIIa, IVa, IVb, Va, or Vb, X is oxygen (O). In other embodiments of compounds of formula III, IIIa, IVa, IVb, Va, or Vb, X is sulfur (S). In still other embodiments of compounds of formula III, IIIa, IVa, IVb, Va, or Vb, X is —(NR8)-, where R8 is independently selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl.

Other preferred embodiments of the invention include compounds of formula III or IIIa, where Q is a heteroaryl or an optionally substituted heteroaryl group. In four separate alternative preferred embodiments of compounds of formula III or IIIa, Q is an optionally substituted monocyclic heteroaryl group, an optionally substituted bicyclic heteroaryl group, an optionally substituted bicyclic heteroaryl group with the proviso that the bicyclic heteroaryl group is not an indolyl group or a substituted indolyl, or an optionally substituted tricyclic heteroaryl group. Optional substituents, when present, are independently selected from those recited for aryl, heteroaryl, —O-aryl, —S-aryl, —O-heteroaryl, and —S-heteroaryl.

Included in the preferred embodiments of the invention are compounds of formula IVa, IVb, Va, or Vb, where Q is a heteroaryl or an optionally substituted heteroaryl group. In four separate alternative preferred embodiments of compounds of formula IVa, IVb, Va, or Vb, Q is an optionally substituted monocyclic heteroaryl group, an optionally substituted bicyclic heteroaryl group, an optionally substituted bicyclic heteroaryl group with the proviso that the bicyclic heteroaryl group is not indolyl, or an optionally substituted tricyclic heteroaryl group. In a more preferred embodiment, Q is an optionally substituted nitrogen-containing heteroaryl group. In a related embodiment, Q is an optionally substituted indolyl. Optional substituents, when present are independently selected from those recited for aryl, heteroaryl, —O-aryl, —S-aryl, —O-heteroaryl, and —S-heteroaryl.

Preferred embodiments of the invention include mixtures of compounds of formula IVa and IVb, including racemic mixtures. In another preferred embodiment, the compounds of formula IVa and IVb are the separate enantiomers of (±)-cis-3-(5,6-dihydro-4H-pyrrolo[3,2,1-ij]quinolin-1-yl)-4-(1H-indol-3-yl)pyrrolidine-2,5-dione. In this embodiment the preparation of (±)-cis-3-(5,6-dihydro-4H-pyrrolo[3,2,1-ij]quinolin-1-yl)-4-(1H-indol-3-yl)pyrrolidine-2,5-dione is prepared as a mixture beginning with the starting materials 1,2,3,4-tetrahydroquinoline and indole-3-acetamide. The 1,2,3,4-tetrahydroquinoline is converted into 5,6-dihydro-4H-pyrrolo[3,2,1-ij]quinolin-1-yl)oxoacetic acid methyl ester as described in Example 1, steps 1-5. The 5,6-dihydro-4H-pyrrolo[3,2,1-ij]quinolin-1-yl)oxoacetic acid methyl ester is reacted with indole-3-acetamide as described in Example 1, step 6, to yield 3-(5,6-dihydro-4H-pyrrolo[3,2,1-ij]quinolin-1-yl)-4-(1H-indol-3-yl)pyrrole-2,5-dione. The mixture of (±)-cis-3-(5,6-dihydro-4H-pyrrolo[3,2,1-ij]quinolin-1-yl)-4-(1H-indol-3-yl)pyrrolidine-2,5-dione is then prepared by catalytic hydrogenation as described in Example 2 using Procedure B.

Preferred embodiments of the invention also include mixtures of compounds of formula Va and Vb, including racemic mixtures. In another preferred embodiment, the compounds of Va and Vb are the separate enantiomers of (±)-trans-3-(5,6-dihydro-4H-pyrrolo[3,2,1-ij]quinolin-1-yl)-4-(1H-indol-3-yl)pyrrolidine-2,5-dione. In this embodiment, the compounds are prepared as a mixture by first preparing (±)-cis-3-(5,6-dihydro-4H-pyrrolo[3,2,1-ij]quinolin-1-yl)-4-(1H-indol-3-yl)pyrrolidine-2,5-dione, as described above. The mixture of cis compounds is then treated with a mixture of potassium tert-butoxide in tert-butanol to obtain a mixture of (±)-trans-3-(5,6-dihydro-4H-pyrrolo[3,2,1-ij]quinolin-1-yl)-4-(1H-indol-3-yl)pyrrolidine-2,5-dione as described in Example 3.

All stereoisomers of the compounds of the instant invention are contemplated, either in admixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as $Na^+$, $K^+$, $Li^+$, alkali earth metal salts such as Mg or Ca, or organic amine salts.

As used herein, the term "metabolite" means a product of metabolism of a compound of formula III, IIIa, IVa, IVb, Va, or Vb, or a pharmaceutically acceptable salt, analog or derivative thereof, that exhibits a similar activity in vivo to said a compound of formula III, IIIa, IVa, IVb, Va, or Vb.

As used herein, the term "prodrug" means a compound of formula III, IIIa, IVa, IVb, Va, or Vb covalently linked to one or more pro-moieties, such as an amino acid moiety or other water solubilizing moiety. A compound of formula III, IIIa, IVa, IVb, Va, or Vb may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake.

3. The Pharmaceutical Compositions and Formulations

A pharmaceutical composition of the invention is formulated to be compatible with its intended route of administration. Examples of routes of administration include parenteral, e.g., intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

Preferably, (−)-trans-3-(5,6-dihydro-4H-pyrrolo[3,2,1-ij] quinolin-1-yl)-4-(1H-indol-3-yl)pyrrolidine-2,5-dione is administered at dosage of 360 mg, twice a day, for a maximal daily dosage of 720 mg. (−)-trans-3-(5,6-dihydro-4H-pyrrolo [3,2,1-ij]quinolin-1-yl)-4-(1H-indol-3-yl)pyrrolidine-2,5-dione is optionally administered to subjects or patients at an initial dosage of 10 mg twice daily for a maximal daily dose of 20 mg, with dosage escalation to administration of 360 mg twice daily for a maximal daily dosage of 720 mg. Preferred dosage forms of (−)-trans-3-(5,6-dihydro-4H-pyrrolo[3,2,1-ij]quinolin-1-yl)-4-(1H-indol-3-yl)pyrrolidine-2,5-dione include, but are not limited to, caplets, tablets, pills, and freeze-dried powder. For instance, a subject or patient is administered one 360 mg caplet twice a day, or alternatively, two 180 mg caplets, twice a day, for a maximal daily dosage of 720 mg. (−)-trans-3-(5,6-dihydro-4H-pyrrolo[3,2,1-ij] quinolin-1-yl)-4-(1H-indol-3-yl)pyrrolidine-2,5-dione caplets or tablets are also formulated in 60 mg doses.

The pharmaceutical compositions can include co-formulations of any of the compounds described herein.

The pharmaceutical compositions can be included in a container, pack, or dispenser together with instructions for administration.

EXAMPLES

Examples are provided below to further illustrate different features of the present invention. The examples also illustrate useful methodology for practicing the invention. These examples do not limit the claimed invention.

Examples of preparation of a compound of formula III, IIIa, IVa, IVb, Va or Vb (including (+)-cis-3-(5,6-dihydro-4H-pyrrolo[3,2,1-ij]quinolin-1-yl)-4-(1H-indol-3-yl)pyrrolidine-2,5-dione, (−)-cis-3-(5,6-dihydro-4H-pyrrolo[3,2,1-ij]quinolin-1-yl)-4-(1H-indol-3-yl)pyrrolidine-2,5-dione, (+)-trans-3-(5,6-dihydro-4H-pyrrolo[3,2,1-ij]quinolin-1-yl)-4-(1H-indol-3-yl)pyrrolidine-2,5-dione, and (−)-trans-3-(5,6-dihydro-4H-pyrrolo[3,2,1-ij]quinolin-1-yl)-4-(1H-indol-3-yl)pyrrolidine-2,5-dione) and use thereof, either alone or in combination with a therapeutically effective amount of a second anti-proliferative agent, are described in international application PCT/US2010/023893, which is incorporated by reference in its entirety for all purposes.

Examples

Materials and Methods

Unless otherwise stated, the following materials and methods apply to the biological assays described herein.

Cell culture and reagents: AN3 CA, ASPC-1, MDA-MB-231, NCI-H1229, SK-OV-3 and Panc-1 cancer cell lines (American Type Culture Collection) were cultured in Dulbecco's modified Eagle's medium containing 10% fetal bovine serum, 100 units/mL penicillin, 100 μg/mL streptomycin, and 2 mM L-glutamine.

Isobologram analysis: For each cell line and drug combination, the 72 hour $IC_{50}$ values were determined for each individual drug and in combination at the equipotent fixed ratio by MTT proliferation endpoint assay or by colony formation assay. For example, in the case of drugs A and B, where the $IC_{50}$ values are 1 μM and 5 μM, respectively, the equipotent ratio is 1:5. Therefore, a serial dilution of the highest combination concentration (8× to 0.125×, where X is the $IC_{50}$ ratio concentration) was used to generate a dose response curve. The degree of inhibition of cell proliferation in this assay relative to unexposed controls was designated the "effect", which ranged from 0.0 (no inhibition) to 1.0 (no cellular conversion of the MTT or MTS reagent, denoting complete cell death). Duplicate independent experiments were performed for each cell line/drug combination. Data were then analyzed by Calcusyn™ (Biosoft, Cambridge, UK) data analysis software.

Combination Index. Two independent experiments were performed in parallel. The Chou algorithm was employed to calculate the Combination Index (CI) which is shown in Table 1.

TABLE 1

| Criteria for Combination Index (CI) | |
|---|---|
| CI ≤ 0.3 | Strong Synergy |
| 0.3 < CI ≤ 0.85 | Synergy |
| 0.85 < CI ≤ 1.2 | Additive |
| 1.2 < CI ≤ 3.3 | Antagonism |
| CI ≥ 3.3 | Strong Antagonism |

Figures 2, 10A:
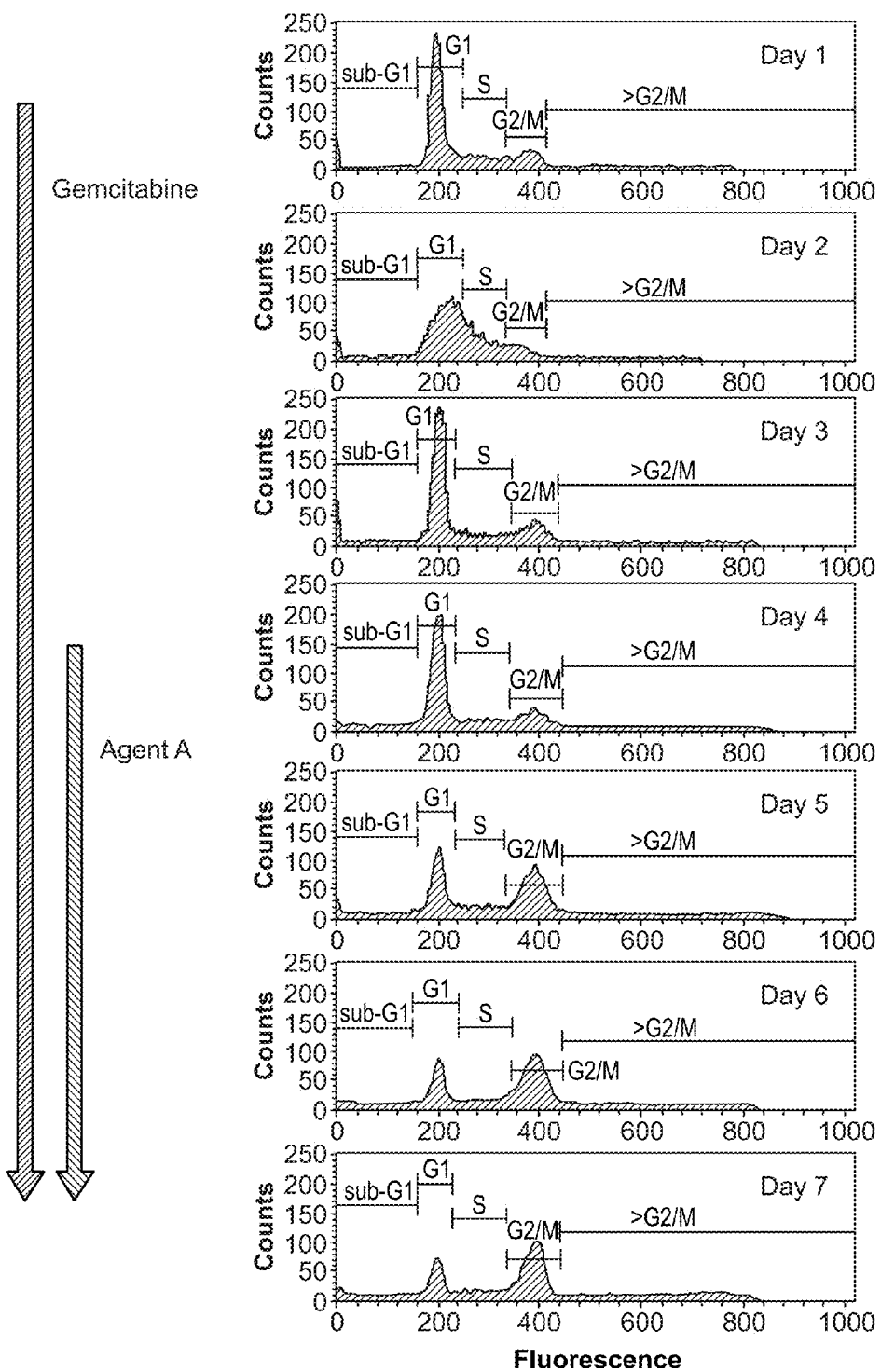
FIG. 10 shows cell cycle analysis of MDA-MB-231 cells (Panels A and B) following gemcitabine and (−)-trans-3-(5, 6-dihydro-4H-pyrrolo[3,2,1-ij]quinolin-1-yl)-4-(1H-indol-3-yl)pyrrolidine-2,5-dione treatment as shown. Panels C and D show immunoblots of the MDA-MB-231 cells (from the studies in Panels A and B, respectively) using anti-phospho-Chk1, phospho-histone H3 (Ser10) and beta-actin antibodies
Figures 2, 10B:
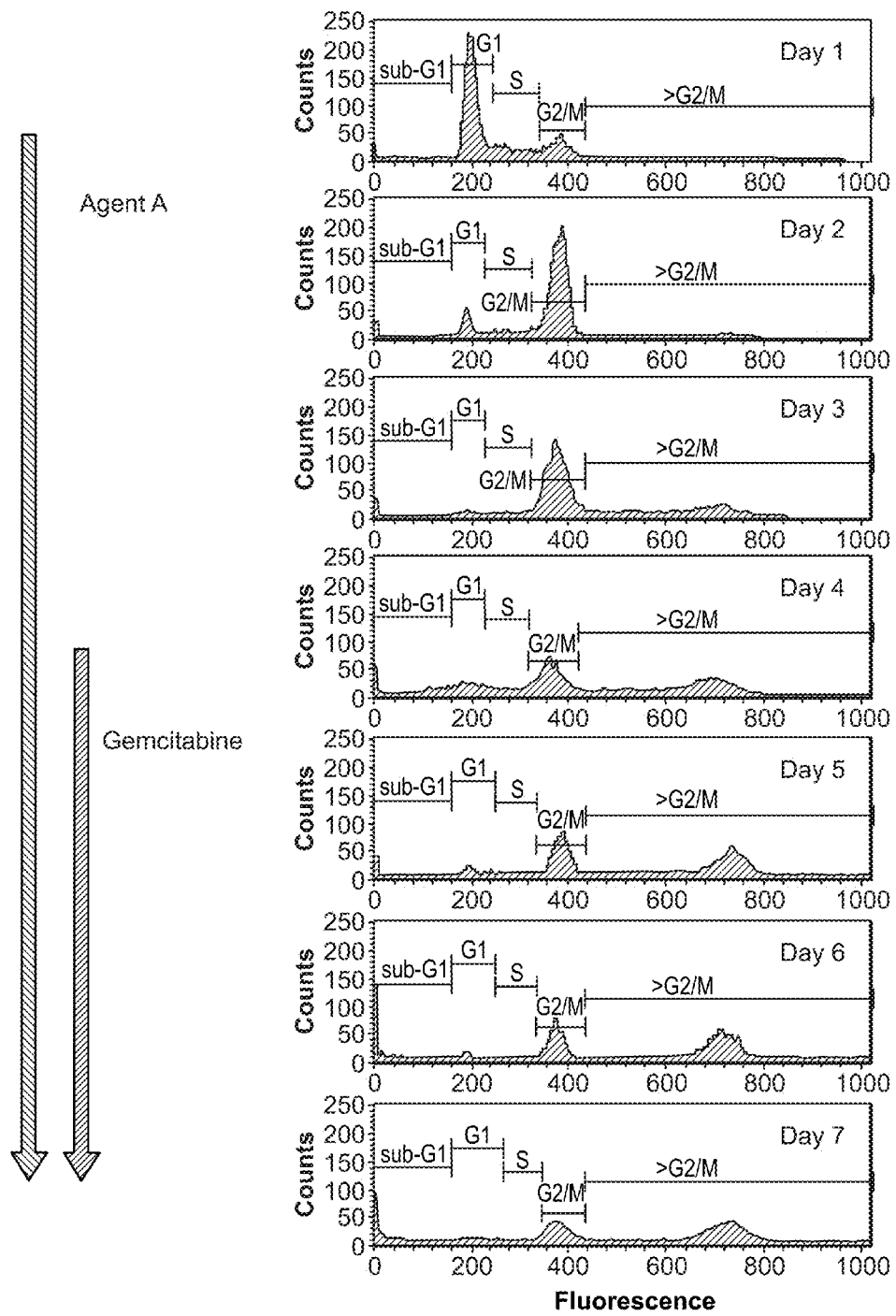
Figure 10C:
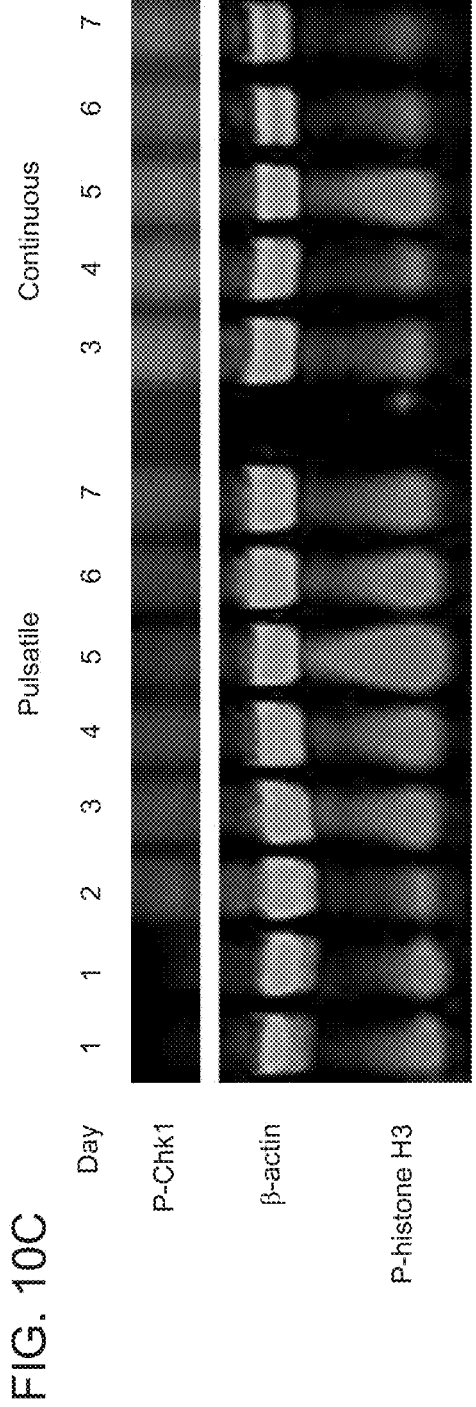
Figure 10D:
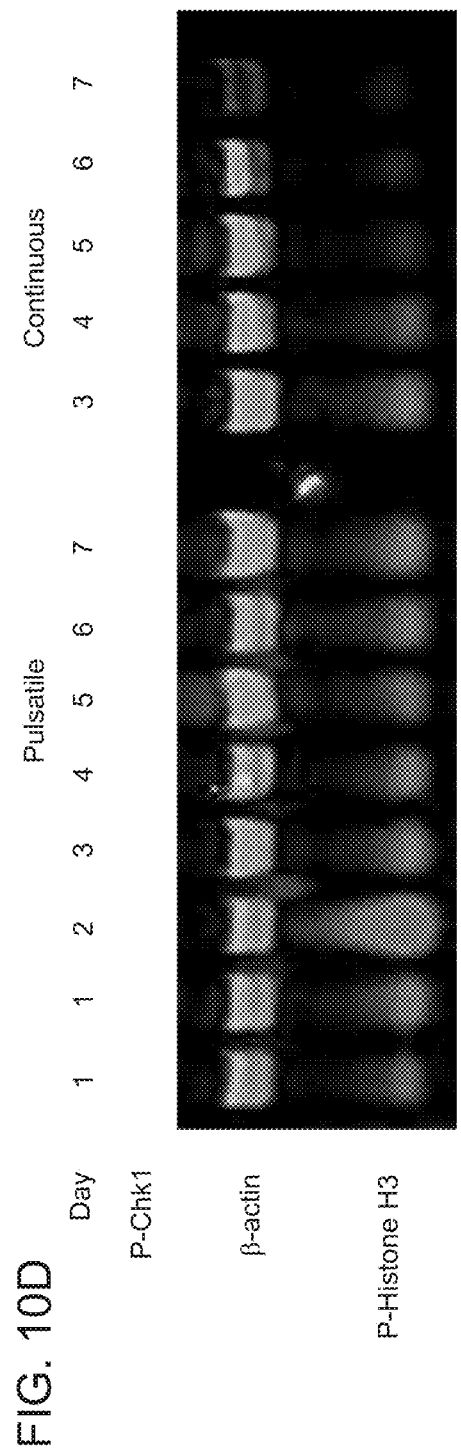

Combination indices were determined according to the method of Chou. (Chou, T.-C. 1991. The median-effect principle and the combination index for quantitation of synergism and antagonism, p. 61-102. In T.-C. Chou and D. C. Rideout (ed.), Synergism and antagonism in chemotherapy. Academic Press, San Diego, Calif.). FIG. 2, panel A, shows where $C_A^0$ and $C_B^0$ are the separate concentrations of drug A and B respectively that achieve the same effect as the mixture of drug A and of drug B. Isobologram analyses categorized drug combinations as synergistic, additive, or antagonistic. Specifically, FIG. 2, panel B, shows isobologram analyses for a particular effect (e.g., 50% of the maximum) in which the dose of drug A alone is A=20 and drug B alone is B=100. The straight line connecting these intercept points is the additivity line which, based on these potencies, should give the same effect. An actual dose pair such as point Q attains this effect with lesser quantities and is supra-additive or synergistic, while the dose pair denoted by point R means greater quantities are required and is therefore sub-additive. A point such as P that appears below the line would be simply additive.

Cell survival analysis. In some experiments, cell survival was determined by the 3-(4,5-dimethylthiazol-2-yl)-2,5-diphenyl tetrazolium bromide (MTT) assay. Briefly, cells were plated in a 96-well plate at 5-10,000 cells per well, cultured for 24 hours in complete growth medium, and then treated with various drugs and drug combinations for 72 hours. MTT was added to a final concentration of 0.5 mg/mL, and incubated for 1 hour, followed by assessment of cell viability using the microplate reader at 570 nm. Data were normalized to untreated controls and analyzed with Microsoft Excel.

Cell proliferation assay. Exponentially growing cells were seeded at 2,000 cells per well in 6-well plates and allowed to attach for 24 hours. Increasing concentrations of individual drugs and those in combination were then added to the media for another 24 hours. After 24 hours exposure, the drug was removed and fresh media was added for the next 14-21 days, allowing for colony formation. Cells were fixed and stained with GIEMSA (Gibco BRL). Colonies of greater than 50 cells were scored as survivors and the percentage of cell survival was plotted to determine the $IC_{50}$ values.

Gemcitabine and (−)-trans-3-(5,6-dihydro-4H-pyrrolo[3,2,1-ij]quinolin-1-yl)-4-(1H-indol-3-yl)pyrrolidine-2,5-dione both induce cell cycle arrest in cancer cells, but in different phases. Gemcitabine induces a G1/S phase arrest, resulting in the essential synchronization and an accumulation of the cell population in the G1/S phase. (−)-trans-3-(5,6-dihydro-4H-pyrrolo[3,2,1-ij]quinolin-1-yl)-4-(1H-indol-3-yl)pyrrolidine-2,5-dione arrests cells in the G2/M phase of the cell cycle. A standard anchorage-dependent MTS cytotoxicity assay was modified and extended to seven days to test the enhanced anti-proliferative activity of (−)-trans-3-(5,6-dihydro-4H-pyrrolo[3,2,1-ij]quinolin-1-yl)-4-(1H-indol-3-yl)pyrrolidine-2,5-dione in combination with gemcitabine.

The modified MTS assay is shown in FIG. 3. Cells were plated on day 0. In schedules A and C, the first of the two agents (i.e., (−)-trans-3-(5,6-dihydro-4H-pyrrolo[3,2,1-ij]quinolin-1-yl)-4-(1H-indol-3-yl)pyrrolidine-2,5-dione, identified as Agent A, and gemcitabine) was introduced to the cells on day 2 for a 24 hour period, followed by a wash-out of the first agent on day 3. The cells were incubated without the first agent for 48 hours before the second agent was introduced on day 5. The cells were incubated with the second agent for 24 hours before the second agent was washed out on day 6. The cells were further incubated without the second agent until the MTS assay was performed on day 8 or 9. In schedules B and D, no wash-out of either the first or the second agent was conducted.

Example 1

Combination of c-Met Inhibitors with Gemcitabine for the Treatment of Various Anti-Proliferative Disorders and Cancer Gemcitabine and (−)-trans-3-(5,6-dihydro-4H-pyrrolo[3,2,1-ij]quinolin-1-yl)-4-(1H-indol-3-yl)pyrrolidine-2,5,-dione were given in various pulsatile schedules as shown in FIG. 3. The cancer cells were more susceptible to the anti-proliferative effects of the two agents if the cancer cells were not exposed to the two agents together, i.e., when there was no wash-out of the two agents.

In a variety of formats when both gemcitabine and (−)-trans-3-(5,6-dihydro-4H-pyrrolo[3,2,1-ij]quinolin-1-yl)-4-(1H-indol-3-yl)pyrrolidine-2,5,-dione were either combined at the same time, or when no wash-out was conducted, these two agents were frequently antagonistic. The present invention converted this antagonistic effect to, at the minimum, an additive effect, and in many cases, a synergistic effect.

The combination data of (−)-trans-3-(5,6-dihydro-4H-pyrrolo[3,2,1-ij]quinolin-1-yl)-4-(1H-indol-3-yl)pyrrolidine-2,5-dione with gemcitabine under continuous dosing conditions are shown in Table 2.

TABLE 2

| Human Cancer Cell Line | Tissue of Origin | Combination Index | Classification |
|---|---|---|---|
| RT4 | Bladder | 1.10 | Additive |
| HCI-H526 | Lung | 1.11 | Additive |
| SNU398 | Liver | 1.15 | Additive |
| SNU-16 | Gastric | 1.16 | Additive |
| LOVO | Colon | 1.19 | Additive |
| U937 | Blood | 1.21 | Antagonism |
| SK-HEP1 | Liver | 1.23 | Antagonism |
| HCT-116 | Colon | 1.26 | Antagonism |
| ASPC-1 | Pancreas | 1.27 | Antagonism |
| KG-1a | Blood | 1.28 | Antagonism |
| 786-O | Kidney | 1.29 | Antagonism |
| THP-1 | Blood | 1.31 | Antagonism |
| KG-1 | Blood | 1.32 | Antagonism |
| NCI-H1299 | Lung | 1.33 | Antagonism |
| RT112 | Bladder | 1.39 | Antagonism |
| DU145 | Prostate | 1.41 | Antagonism |
| DU4475 | Breast | 1.42 | Antagonism |
| CAKI-1 | Kidney | 1.42 | Antagonism |
| CCS-292 | Soft Tissue | 1.46 | Antagonism |
| A549 | Lung | 1.47 | Antagonism |
| SK-LMS-1 | Vulva | 1.50 | Antagonism |
| DLD-1 | Colon | 1.51 | Antagonism |
| NCI-H520 | Lung | 1.51 | Antagonism |
| HT29 | Colon | 1.57 | Antagonism |
| WM-266.4 | Skin | 1.63 | Antagonism |
| U266 | Blood | 1.64 | Antagonism |
| COLO-205 | Colon | 1.67 | Antagonism |
| K562 | Blood | 1.67 | Antagonism |
| HEP-3B | Liver | 1.68 | Antagonism |
| BX-PC3 | Pancreas | 1.72 | Antagonism |
| LS411N | Colon | 1.74 | Antagonism |
| HL-60 | Blood | 1.76 | Antagonism |
| NCI-H460 | Lung | 1.87 | Antagonism |
| BDCM | Blood | 1.91 | Antagonism |
| NCI-H1993 | Lung | 1.93 | Antagonism |
| Jurkat | Blood | 1.99 | Antagonism |
| MDA MB-231 | Breast | 2.31 | Antagonism |
| SNU-387 | Liver | 3.90 | Antagonism |
| NCI-H661 | Lung | 4.08 | Antagonism |
| PANC-1 | Pancreas | 5.20 | Antagonism |

Tables 3 and 4 show the comparison between continuous dosing and pulsatile dosing with drug free periods. The compound (−)-trans-3-(5,6-dihydro-4H-pyrrolo[3,2,1-ij]quinolin-1-yl)-4-(1H-indol-3-yl)pyrrolidine-2,5,-dione is identified as "Agent A" in these tables. The identity and tissue origin of cancer cell lines are indicated. "Gemcitabine→Agent A" indicates that Agent A is administered after gemcitabine and "Agent A→Gemcitabine" shows that gemcitabine is administered after Agent A.

FIGS. 4-7 show isobologram analysis of gemcitabine and (−)-trans-3-(5,6-dihydro-4H-pyrrolo[3,2,1-ij]quinolin-1-yl)-4-(1H-indol-3-yl)pyrrolidine-2,5-dione treatment in AN3 CA (Panel A), ASPC-1 (Panel B), MDA-MB-231 (Panel C) and NCI-H1299 (Panel D) cells. Specifically, FIG. 4 shows the isobolograms of gemcitabine treatment followed by (−)-trans-3-(5,6-dihydro-4H-pyrrolo[3,2,1-ij]quinolin-1-yl)-4-(1H-indol-3-yl)pyrrolidine-2,5-dione treatment with wash-

TABLE 3

| | | Gemcitabine → Agent A | | | | Agent A → Gemcitabine | | | |
| | | Intervening Wash | | No Wash | | Intervening Wash | | No Wash | |
| Cancer Cell Line | Tissue Type | CI | Effect | CI | Effect | CI | Effect | CI | Effect |
|---|---|---|---|---|---|---|---|---|---|
| NCI-H1299 | NSCLC (Non Small cell Lung) | 0.87 | additive | 1.25 | antagonism | 1.05 | additive | 1.25 | antagonism |
| AsPC-1 | Pancreas | 0.43 | synergism | 1.47 | antagonism | 1.68 | antagonism | 1.27 | antagonism |
| MDA-MB-231 | Breast | 0.41 | synergism | 1.52 | antagonism | 1..01 | additive | 2.04 | antagonism |
| AN3 CA | Uterus | 0.66 | synergism | 1.36 | antagonism | 0.79 | synergism | 1.96 | antagonism |

In Table 4 a score of ≤0.8 is indicative of a synergistic effect, a score of >0.85-≤1.2 is indicative of an additive effect and a score of >1.2-≤3.3 is indicative of an antagonistic effect.

In the "Concurrent" dosing regimen, cells were treated with gemcitabine and Agent A simultaneously for 72 hrs before being subjected to the MTS cell proliferation assay.

In the "Sequential-Continuous" dosing regimen, cells were treated with a first agent (gemcitabine or Agent A) alone for the time interval indicated followed by treatment a second agent (the opposite of the first agent) without removing the first agent. Cells were cultured with both compounds for the indicated time interval before being subjected to the MTS cell proliferation assay. Specifically, Continuous I indicates administration of the first agent for a 24 hour period followed by administration of the second agent (without removing the first agent) for a 48 hour period. Continuous II indicates administration of the first agent for a 48 hour period followed by administration of the second agent (without removing the first agent) for a 48 hour period. Continuous II indicates administration of the first agent for a 72 hour period followed by administration of the second agent (without removing the first agent) for a 96 hour period.

In the "Sequential-Pulsatile" dosing regimen, cells were treated with a first agent (gemcitabine or Agent A) alone for 24 hours followed by continuous culture in drug-free medium. Cells were then given 0, 24 or 48 hours of a drug-free period before treatment with a second agent (the opposite of the first agent) for 24 hours. Cells were then given additional 24 or 72 hours drug-free culture before being subjected to the MTS cell proliferation assay. Specifically, Pulsatile I indicates administration of the first agent for a 24 hour period followed by 0 hours of a drug-free period followed by administration of a second agent for 24 hours followed by 24 hours of a drug-free period. Pulsatile I indicates administration of the first agent for a 24 hour period followed by 24 hours of a drug-free period followed by administration of a second agent for 24 hours followed by 24 hours of a drug-free period. Pulsatile III indicates administration of the first agent for a 24 hour period followed by 48 hours of a drug-free period followed by administration of a second agent for 24 hours followed by 72 hours of a drug-free period.

out of gemcitabine. FIG. 5 shows the isobolograms of gemcitabine treatment followed by (−)-trans-3-(5,6-dihydro-4H-pyrrolo[3,2,1-ij]quinolin-1-yl)-4-(1H-indol-3-yl)pyrrolidine-2,5-dione treatment without wash-out of gemcitabine. FIG. 6 shows the isobolograms of (−)-trans-3-(5,6-dihydro-4H-pyrrolo[3,2,1-ij]quinolin-1-yl)-4-(1H-indol-3-yl)pyrrolidine-2,5-dione treatment followed by gemcitabine treatment with wash-out of (−)-trans-3-(5,6-dihydro-4H-pyrrolo[3,2,1-ij]quinolin-1-yl)-4-(1H-indol-3-yl)pyrrolidine-2,5-dione. FIG. 7 shows the isobolograms of (−)-trans-3-(5,6-dihydro-4H-pyrrolo[3,2,1-ij]quinolin-1-yl)-4-(1H-indol-3-yl)pyrrolidine-2,5-dione treatment followed by gemcitabine treatment without wash-out of (−)-trans-3-(5,6-dihydro-4H-pyrrolo[3,2,1-ij]quinolin-1-yl)-4-(1H-indol-3-yl)pyrrolidine-2,5-dione.

Figure 9:
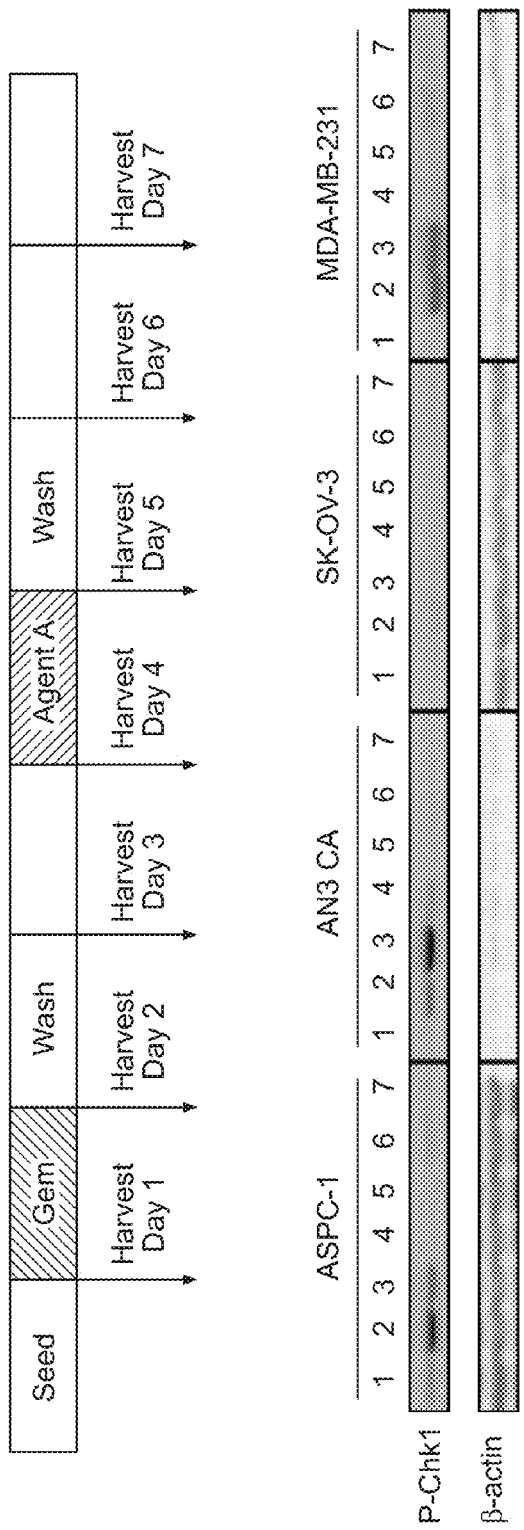
FIG. 9 shows activation of cell cycle check point by gemcitabine during dosing regimen A presented in FIG. 3.

FIG. 8 is a cell cycle analysis of dosing regimen A presented in FIG. 3, showing S-phase arrest in response to gemcitabine treatment and G2/M arrest in response to (−)-trans-3-(5,6-dihydro-4H-pyrrolo[3,2,1-ij]quinolin-1-yl)-4-(1H-indol-3-yl)pyrrolidine-2,5-dione treatment. FIG. 9 shows activation of cell cycle check point by gemcitabine during dosing regimen A presented in FIG. 3.

FIG. 10 shows cell cycle analysis of MDA-MB-231 cells (A and B) following gemcitabine and (−)-trans-3-(5,6-dihydro-4H-pyrrolo[3,2,1-ij]quinolin-1-yl)pyrrolidine-2,5-dione treatment as shown.

Specifically, the MDA-MB-231 cells were treated with 0.4 mM of gemcitabine and 3.3 mM of (−)-trans-3-(5,6-dihydro-4H-pyrrolo[3,2,1-ij]quinolin-1-yl)-4-(1H-indol-3-yl)pyrrolidine-2,5-dione using the indicated dosing regimens. Samples were collected at the indicated time points and subjected to flow cytometric analysis. Studies were also conducted with A549 cells with similar results.

A fraction of MDA-MB-231 cells were collected from the experiment conducted in Panels A and B and were lysed and subjected to immunoblotting analysis using anti-phospho-Chk1, phospho-histone H3 (Ser10) and b-actin antibodies as shown in FIG. 10, Panels C and D, respectively.

TABLE 4

| Cell Line Tissue Origin | A549 Lung | NCK-H1299 Lung | RT4 Bladder | RT112 Bladder | ASPC-1 Pancreas | PANC-1 Pancreas | MDA-MB-231 Breast | MDA-MB-468 Breast | SV-OV-3 Ovary | A2780 Ovary | AN3 CA Uterus | NOZ Gall Bladder |
|---|---|---|---|---|---|---|---|---|---|---|---|---|
| GEM + Agent A Concurrently | 1.3 | 1.8 | 1.3 | 2.0 | 4.7 | 6.5 | ND | 2.2 | 2.2 | 1.7 | 4.0 | 2.5 |
| GEM → Agent A Continuous I | 1.2 | 1.8 | 1.7 | 1.9 | 5.1 | 1.7 | 0.4 | 1.6 | 2.2 | 1.4 | 2.2 | 0.3 |
| GEM → Agent A Continuous II | 1.3 | 1.7 | ND | 1.4 | 1.6 | ND | 1.1 | 1.8 | 1.6 | 1.5 | 1.3 | 0.5 |
| GEM → Agent A Continuous III | 1.1 | 1.3 | 1.9 | 1.2 | 1.2 | 1.4 | 1.2 | 1.7 | 1.4 | 1.2 | 1.3 | 1.1 |
| GEM → Agent A Pulsatile I | 1.0 | 1.5 | 1.1 | 2.1 | 4.1 | ND | 9.1 | 0.1 | 2.2 | 1.3 | 10.3 | 2.0 |
| GEM → Agent A Pulsatile II | 1.3 | 1.0 | 1.2 | 1.3 | 0.5 | ND | 1.6 | 1.3 | 1.6 | 1.5 | 0.7 | 0.6 |
| GEM → Agent A Pulsatile III | 0.7 | 1.0 | 1.2 | 1.0 | 0.6 | 1.1 | 0.6 | 1.2 | 0.8 | 1.1 | 0.9 | 0.7 |
| Agent A → GEM Continuous I | 2.0 | 4.4 | 3.8 | ND | 1.4 | 0.8 | 0.5 | 1.5 | 2.2 | 1.7 | 2.8 | 0.3 |
| Agent A → GEM Continuous II | 1.9 | ND | ND | ND | ND | 1.3 | ND | 1.3 | ND | 1.6 | ND | 0.1 |
| Agent A → GEM Continuous III | 1.5 | 1.3 | 2.0 | 1.9 | 1.3 | 1.4 | 1.5 | 1.8 | 0.7 | 1.5 | 1.6 | 1.0 |
| Agent A → GEM Pulsatile I | 3.8 | 3.4 | 1.9 | ND | 2.0 | 0.7 | 0.4 | 1.6 | 2.2 | 1.7 | 2.1 | 1.5 |
| Agent A → GEM Pulsatile II | 1.3 | ND | 1.4 | ND | 1.0 | 0.2 | 0.6 | 1.2 | 0.4 | 1.4 | ND | 0.8 |
| Agent A → GEM Pulsatile III | 0.8 | 1.4 | 1.3 | 1.0 | 1.3 | 0.9 | 0.8 | 1.1 | 1.0 | 0.9 | 0.8 | 0.8 |

Example 2

In Vivo Study

In a one-week schedule, after a drug-free period, gemcitabine was administered to a patient at a dose of 1000 mg/m$^2$ daily. The gemcitabine treatment was followed by another drug-free period. Agent A was then administered to the patient at 360 mg twice daily for 4 days. Cytotoxic potentiation between gemcitabine and agent A was followed both in vitro and in vivo and was confirmed in appropriate xenograft models.

What is claimed is:

1. A method of treating a cell proliferative disorder in a subject in need thereof, comprising administering to a subject a therapeutically effective amount of (−)-trans-3-(5,6-dihydro-4H-pyrrolo[3,2,1-ij]quinolin-1-yl)-4-(1H-indol-3-yl) pyrrolidine-2,5-dione or a pharmaceutically acceptable salt thereof, in combination with a therapeutically effective amount of a second anti-proliferative agent, wherein the second anti-proliferative agent is gemcitabine wherein (−)-trans-3-(5,6-dihydro-4H-pyrrolo[3,2,1-ij]quinolin-1-yl)-4-(1H-indol-3-yl)pyrrolidine-2,5-dione or a pharmaceutically acceptable salt thereof and said second anti-proliferative agent are not administered concurrently, and wherein the cell proliferative disorder is non-small cell lung cancer, breast cancer, pancreatic cancer, uterine cancer, bladder cancer, lung cancer, liver cancer, gastric cancer or colon cancer.

2. The method of claim 1, wherein gemcitabine is administered through continuous intravenous or intraperitoneal administration for no more than 30 minutes.

3. The method of claim 1, wherein gemcitabine is administered through continuous intravenous or intraperitoneal administration for no more than 1 hour.

4. The method of claim 1, wherein gemcitabine is administered through continuous intravenous or intraperitoneal administration for no more than 12 hours.

5. The method of claim 1, wherein gemcitabine is administered through continuous intravenous or intraperitoneal administration for no more than 24 hours.

6. The method of claim 1, wherein (−)-trans-3-(5,6-dihydro-4H-pyrrolo[3,2,1-ij]quinolin-1-yl)-4-(1H-indol-3-yl) pyrrolidine-2,5-dione is administered for 24 hours to 96 hours.

7. The method of claim 1, wherein (−)-trans-3-(5,6-dihydro-4H-pyrrolo[3,2,1-ij]quinolin-1-yl)-4-(1H-indol-3-yl) pyrrolidine-2,5-dione is administered for 48 hours to 96 hours.

8. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered for 72 hours to 96 hours.

9. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered at least 12 hours after the end of gemcitabine administration.

10. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered at least 24 hours after the end of gemcitabine administration.

11. The method of claim 1, wherein neither said second anti-proliferative agent nor (−)-trans-3-(5,6-dihydro-4H-pyrrolo[3,2,1-ij]quinolin-1-yl)-4-(1H-indol-3-yl)pyrrolidine-2,5-dione is administered for at least 12 hours before the start of gemcitabine administration.

12. The method of claim 1, wherein neither said second anti-proliferative agent nor (−)-trans-3-(5,6-dihydro-4H-pyrrolo[3,2,1-ij]quinolin-1-yl)-4-(1H-indol-3-yl)pyrrolidine-2,5-dione is administered for at least 24 hours before the start of gemcitabine administration.

13. The method of claim 1, wherein neither said second anti-proliferative agent nor (−)-trans-3-(5,6-dihydro-4H-pyrrolo[3,2,1-ij]quinolin-1-yl)-4-(1H-indol-3-yl)pyrrolidine-2,5-dione is administered for at least 48 hours before the start of gemcitabine administration.

14. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered after the concentration or amount of gemcitabine in said subject is less than about 50% of its concentration or amount at the end of gemcitabine administration.

15. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered after the concentration or amount of gemcitabine in said subject is less than about 10% of its concentration or amount at the end of gemcitabine administration.

16. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered after the concentration or amount of gemcitabine in said subject is less than about 5% of its concentration or amount at the end of gemcitabine administration.

17. The method of claim 1, wherein (−)-trans-3-(5,6-dihydro-4H-pyrrolo[3,2,1-ij]quinolin-1-yl)-4-(1H-indol-3-yl)pyrrolidine-2,5-dione is administered after the concentration or amount of gemcitabine in said subject is less than about 1% of its concentration or amount at the end of gemcitabine administration.

* * * * *